US012458361B2

(12) United States Patent
Kandala et al.

(10) Patent No.: US 12,458,361 B2
(45) Date of Patent: Nov. 4, 2025

(54) OCCLUSIVE DEVICES WITH SPIRAL STRUTS FOR TREATING VASCULAR DEFECTS

(71) Applicant: Covidien LP, Mansfield, MA (US)

(72) Inventors: Bala Subramanya Pavan Kumar Kandala, Irvine, CA (US); Mark P. Ashby, Laguna Niguel, CA (US); Harkamaljot S. Kandail, Irvine, CA (US); Sydney L. Ngo, Riverside, CA (US)

(73) Assignee: COVIDIEN LP, Mansfield, MA (US)

( * ) Notice: Subject to any disclaimer, the term of this patent is extended or adjusted under 35 U.S.C. 154(b) by 216 days.

(21) Appl. No.: 18/145,699

(22) Filed: Dec. 22, 2022

(65) Prior Publication Data

US 2024/0206879 A1 Jun. 27, 2024

(51) Int. Cl.
*A61B 17/12* (2006.01)

(52) U.S. Cl.
CPC .................. *A61B 17/12113* (2013.01); *A61B 2017/12054* (2013.01)

(58) Field of Classification Search
CPC .... A61B 17/12113; A61B 2017/12054; A61B 17/1214; A61B 2017/00845; A61B 17/12031; A61B 2017/1205
See application file for complete search history.

(56) References Cited

U.S. PATENT DOCUMENTS

| | | | |
|---|---|---|---|
| 5,674,241 A | 10/1997 | Bley et al. | |
| 6,309,367 B1 | 10/2001 | Boock | |
| 6,682,557 B1 | 1/2004 | Quiachon et al. | |
| 9,597,086 B2 * | 3/2017 | Larsen | A61B 17/12122 |
| 10,342,686 B2 | 7/2019 | Choubey | |
| 2004/0034386 A1 | 2/2004 | Fulton et al. | |
| 2004/0044391 A1 | 3/2004 | Porter | |
| 2004/0087998 A1 | 5/2004 | Lee et al. | |
| 2004/0138736 A1 | 7/2004 | Obara | |
| 2004/0158311 A1 | 8/2004 | Berhow et al. | |
| 2006/0116748 A1 | 6/2006 | Kaplan et al. | |
| 2007/0135904 A1 | 6/2007 | Eidenschink et al. | |

(Continued)

FOREIGN PATENT DOCUMENTS

WO 2013009976 A2 1/2013

OTHER PUBLICATIONS

International Search Report and Written Opinion mailed Jul. 27, 2023, International Application No. PCT/IB2023/054244, 15 pages.

*Primary Examiner* — Sarah A Long
*Assistant Examiner* — James R McGinnity
(74) *Attorney, Agent, or Firm* — Fortem IP LLP

(57) ABSTRACT

Devices for treating vascular defects and associated systems and methods are disclosed herein. In some embodiments, an occlusive device for treating an aneurysm includes an anchor structure extending circumferentially around an opening. A plurality of spiral struts are coupled to the anchor structure and extend over the opening, and a plurality of protrusions extend away from the spiral struts. The spiral struts and the protrusions can both be arranged within a common plane when the occlusive device is in an expanded configuration. When the occlusive device is deployed within the aneurysm and in the expanded configuration, the spiral struts can span the neck of the aneurysm, and the anchor structure can engage the wall of the aneurysm near the neck.

18 Claims, 16 Drawing Sheets

(56) References Cited

U.S. PATENT DOCUMENTS

| | | | |
|---|---|---|---|
| 2010/0160949 A1 | 6/2010 | Takuma | |
| 2011/0046720 A1 | 2/2011 | Shalev et al. | |
| 2015/0005809 A1 | 1/2015 | Ayres et al. | |
| 2015/0005810 A1* | 1/2015 | Center | A61F 2/01 606/200 |
| 2016/0058539 A1 | 3/2016 | Vantassel et al. | |
| 2016/0331382 A1* | 11/2016 | Center | A61B 17/12031 |
| 2017/0273692 A1 | 9/2017 | Choubey | |
| 2017/0273810 A1 | 9/2017 | Choubey et al. | |
| 2017/0367708 A1 | 12/2017 | Mayer et al. | |
| 2019/0133795 A1 | 5/2019 | Choubey | |
| 2019/0192322 A1 | 6/2019 | Choubey et al. | |
| 2019/0223879 A1 | 7/2019 | Jayaraman | |
| 2019/0269534 A1 | 9/2019 | Choubey | |
| 2019/0307457 A1* | 10/2019 | Mai | A61B 17/1214 |
| 2019/0314175 A1 | 10/2019 | Dawson et al. | |
| 2019/0314176 A1 | 10/2019 | Nageswaran et al. | |
| 2019/0314177 A1 | 10/2019 | Alonso et al. | |
| 2019/0314179 A1 | 10/2019 | Nageswaran et al. | |
| 2019/0380852 A1 | 12/2019 | Eker et al. | |
| 2020/0069313 A1 | 3/2020 | Xu et al. | |
| 2020/0281602 A1* | 9/2020 | Walsh | A61B 17/12172 |
| 2020/0323539 A1 | 10/2020 | Mauger et al. | |
| 2021/0244419 A1* | 8/2021 | Lorenzo | A61F 2/90 |
| 2022/0061854 A1 | 3/2022 | Jalgaonkar et al. | |
| 2022/0125567 A1 | 4/2022 | Center et al. | |
| 2023/0404592 A1 | 12/2023 | Nageswaran | |

* cited by examiner

OCCLUSIVE DEVICES WITH SPIRAL STRUTS FOR TREATING VASCULAR DEFECTS

TECHNICAL FIELD

The present technology generally relates to medical devices, and in particular, to occlusive devices for treating vascular defects.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms with coil embolization involves packing the aneurysm sac with metal coils to reduce or disrupt the flow of blood into the aneurysm, thereby enabling a local thrombus or clot to form which fills and ultimately closes off the aneurysm. Although coiling has proven to have better outcomes than surgical clipping for both ruptured and unruptured aneurysms, treating complex aneurysms using conventional coiling is challenging. This is especially true for wide-necked aneurysms because coil segments may protrude from the aneurysm sac through the neck of the aneurysm and into the parent vessel, causing serious complications for the patient.

To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-necked aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual antiplatelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-necked, giant, fusiform, and blister-like aneurysms. However, because they are positioned in the parent vessel, conventional flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have the potential to provide the intra-aneurysmal flow disruption of coiling with the definitive remodeling at the aneurysm-parent vessel interface achieved by intraluminal flow diverters. Endosaccular devices can be mesh devices configured to be deployed completely within the aneurysm sac, with the interstices of the mesh covering the aneurysm neck and reconstructing the aneurysm-parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

Accordingly, there is a need for improved devices, systems, and methods for treating aneurysms and other vascular defects.

SUMMARY

The subject technology is illustrated, for example, according to various aspects described below. These are provided as examples and do not limit the subject technology.

Clause 1. An occlusive device for treating an aneurysm, the occlusive device expandable from a low-profile configuration to an expanded configuration, the occlusive device comprising: an anchor structure extending circumferentially around an opening; a plurality of spiral struts coupled to the anchor structure and extending over the opening; and a plurality of protrusions extending away from the spiral struts, wherein the plurality of spiral struts and protrusions are arranged within a common plane when the occlusive device is in the expanded configuration, and wherein, when the occlusive device is deployed within the aneurysm in the expanded configuration, the plurality of spiral struts span a neck of the aneurysm and the anchor structure engages a wall of the aneurysm near the neck.

Clause 2. The occlusive device of any one of the preceding clauses, wherein the protrusions each have a first end coupled to a respective spiral strut and a second free end.

Clause 3. The occlusive device of any one of the preceding clauses, wherein the protrusions each have a first end coupled to a first spiral strut and a second end coupled to a second spiral strut.

Clause 4. The occlusive device of any one of the preceding clauses, wherein the device is laser-cut or etched from a single flat sheet of material.

Clause 5. The occlusive device of any one of the preceding clauses, wherein the anchor structure comprises a ring-shaped frame that, in the expanded configuration, extends away from the common plane.

Clause 6. The occlusive device of any one of the preceding clauses, wherein the anchor structure extends substantially perpendicular to the common plane.

Clause 7. The occlusive device of any one of the preceding clauses, further comprising a hub, wherein each spiral strut includes a first end region coupled to the hub, and a second end region coupled to the anchor structure.

Clause 8. The occlusive device of any one of the preceding clauses, wherein the second end region of each spiral strut is coupled to a peripheral edge of the anchor structure.

Clause 9. The occlusive device of any one of the preceding clauses, wherein the second end regions of the plurality of spiral struts are spaced apart along the peripheral edge of the anchor structure.

Clause 10. The occlusive device of any one of the preceding clauses, further comprising a detachment element configured to releasably couple the anchor structure and the plurality of spiral struts to a pusher member.

Clause 11. The occlusive device of any one of the preceding clauses, further comprising a hub, wherein the detachment element is coupled to the plurality of spiral struts via the hub.

Clause 12. The occlusive device of any one of the preceding clauses, further comprising an elongate member connecting the detachment element to the hub.

Clause 13. The occlusive device of any one of the preceding clauses, wherein the anchor structure comprises a stent including a plurality of cells.

Clause 14. The occlusive device of any one of the preceding clauses, wherein, when the occlusive device is deployed within the aneurysm, the plurality of spiral struts are contained entirely within the aneurysm.

Clause 15. The occlusive device of any one of the preceding clauses, wherein, when the occlusive device is deployed within the aneurysm, the plurality of spiral struts are configured to exert outwardly directed forces to enhance the engagement between the anchor structure and the wall of the aneurysm.

Clause 16. The occlusive device of any one of the preceding clauses, wherein the anchor structure is integrally formed with the plurality of spiral struts and protrusions as a single unitary component.

Clause 17. An occlusive device for treating an aneurysm, the occlusive device comprising: an anchor structure defining a central opening; a hub; and a plurality of curved struts arranged in a spiral configuration, each of the curved struts having a first end region coupled to the anchor structure and a second end region coupled to the hub such that the plurality of curved struts extend over the central opening when the occlusive device is in a deployed configuration, each of the curved struts having a plurality of protrusions coupled thereto.

Clause 18. The occlusive device of any one of the preceding clauses, wherein, in the deployed configuration, the curved struts and the protrusions are arranged in a common plane.

Clause 19. The occlusive device of any one of the preceding clauses, wherein the anchor structure extends substantially perpendicular to the common plane.

Clause 20. The occlusive device of any one of the preceding clauses, wherein the anchor structure comprises a ring-shaped frame that, in the deployed configuration, extends away from the common plane.

Clause 21. The occlusive device of any one of the preceding clauses, wherein the protrusions each have a first end coupled to a respective curved strut and a second free end.

Clause 22. The occlusive device of any one of the preceding clauses, wherein the protrusions each have a first end coupled to a first curved strut and a second end coupled to a second curved strut.

Clause 23. The occlusive device of any one of the preceding clauses, wherein the device is laser-cut or etched from a single flat sheet of material.

Clause 24. The occlusive device of any one of the preceding clauses, further comprising a hub, wherein each curved strut includes a first end region coupled to the hub, and a second end region coupled to the anchor structure.

Clause 25. The occlusive device of any one of the preceding clauses, wherein the second end region of each curved strut is coupled to a peripheral edge of the anchor structure.

Clause 26. The occlusive device of any one of the preceding clauses, wherein the second end regions of the plurality of curved struts are spaced apart along the peripheral edge of the anchor structure.

Clause 27. The occlusive device of any one of the preceding clauses, further comprising a detachment element configured to releasably couple the anchor structure and the plurality of curved struts to a pusher member.

Clause 28. The occlusive device of any one of the preceding clauses, wherein the detachment element is coupled to the plurality of curved struts via the hub.

Clause 29. The occlusive device of any one of the preceding clauses, further comprising an elongate member connecting the detachment element to the hub.

Clause 30. The occlusive device of any one of the preceding clauses, wherein the anchor structure comprises a stent including a plurality of cells.

Clause 31. The occlusive device of any one of the preceding clauses, wherein, when the occlusive device is deployed within the aneurysm, the plurality of spiral struts are contained entirely within the aneurysm.

Clause 32. The occlusive device of any one of the preceding clauses, wherein, when the occlusive device is deployed within the aneurysm, the plurality of spiral struts are configured to exert outwardly directed forces to enhance the engagement between the anchor structure and a wall of the aneurysm.

Clause 33. The occlusive device of any one of the preceding clauses, wherein the anchor structure is integrally formed with the plurality of curved struts and protrusions as a single unitary component.

Clause 34. A method of treating an aneurysm, the method comprising: introducing an occlusive device at least partially into the aneurysm, wherein the occlusive device comprises an anchor structure coupled to a plurality of spiral struts, each of the spiral struts having at least one protrusion extending therefrom; and expanding the occlusive device such that the plurality of spiral struts extend across a neck of the aneurysm and the anchor structure engages a wall of the aneurysm near the neck.

Clause 35. The method of any one of the preceding clauses, wherein the occlusive device is introduced to the aneurysm via a catheter.

Clause 36. The method of any one of the preceding clauses, wherein the occlusive device is disposed within the catheter in a low-profile configuration, and wherein expanding the occlusive device comprises advancing the occlusive device out of the catheter such that the occlusive device self-expands into an expanded configuration.

Clause 37. The method of any one of the preceding clauses, wherein, when the occlusive device is in the expanded configuration, the plurality of spiral struts lie substantially within a single plane.

Clause 38. The method of any one of the preceding clauses, wherein, when the occlusive device is in the expanded configuration, the plurality of spiral struts conform to a diameter of the neck of the aneurysm.

Clause 39. The method of any one of the preceding clauses, further comprising:

introducing a conduit into the aneurysm, and delivering an embolization element into the aneurysm via the conduit.

Clause 40. The method of any one of the preceding clauses, further comprising retaining the embolization element within the aneurysm via the occlusive device.

Additional features and advantages of the present technology will be set forth in the description below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1A:
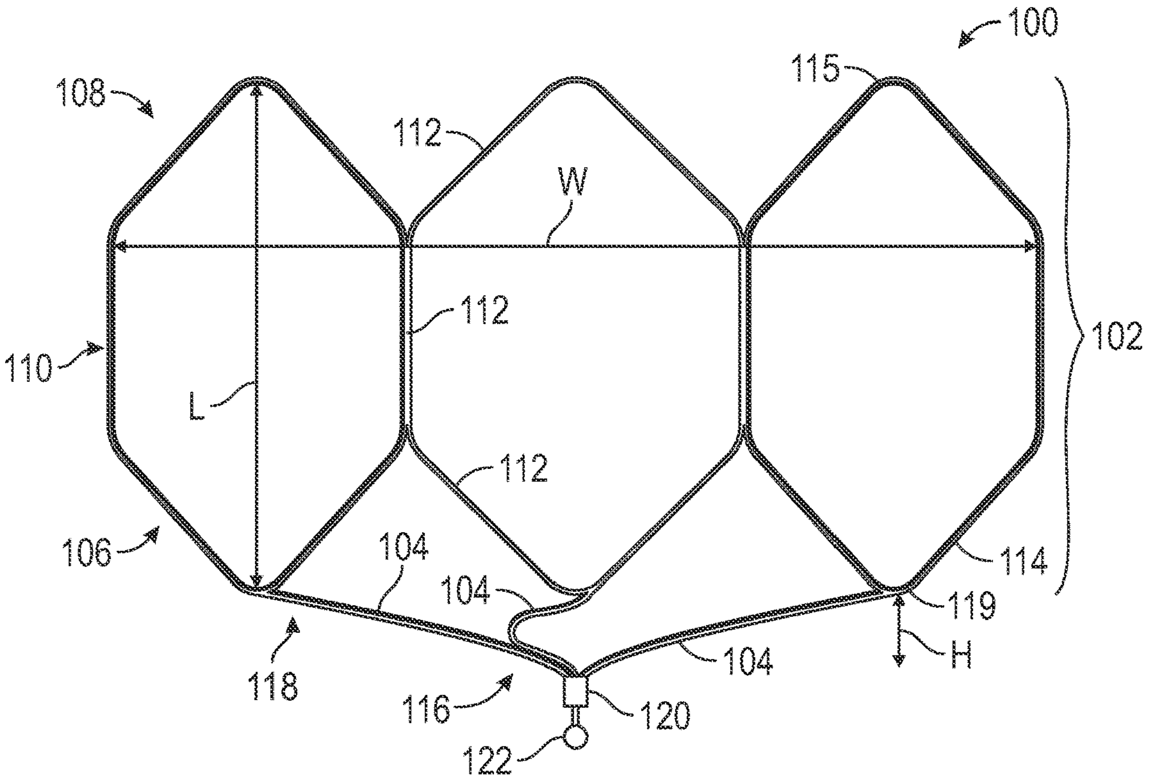
FIG. 1A is a side view of an occlusive device in an expanded configuration, in accordance with embodiments of the present technology.

The present technology relates to devices for treating vascular defects such as aneurysms, and associated systems and methods. In some embodiments, for example, an occlusive device for treating an aneurysm includes an anchor structure (e.g., a tubular or ring-shaped stent or braid) extending circumferentially around an opening. The occlusive device can also include a plurality of spiral struts coupled to the anchor structure and extending over the opening. When the occlusive device is deployed within the aneurysm, the anchor structure and the plurality of spiral struts can self-expand such that the plurality of spiral struts span a neck of the aneurysm and the mesh surface of the anchor structure engages a wall of the aneurysm near the neck. In some embodiments, the occlusive device further includes a plurality of protrusions that extend away from the spiral struts. When the device is in an expanded configuration, the protrusions and spiral struts can be arranged in a common plane. When deployed within an aneurysm, the spiral struts and protrusions can span the neck of the aneurysm, thereby obstructing the flow of blood (or embolic material such as coils, liquid embolics, etc.) into or out of the aneurysm.

The occlusive devices of the present technology can provide many advantages compared to conventional device for treating an aneurysm. For example, the use of spiral struts enables the occlusive device to expand outward to conform to different neck geometries, while keeping the struts substantially in-plane with the aneurysm neck and/or out of the parent vessel. Accordingly, the occlusive devices disclosed herein can be used to treat a wider range of aneurysm sizes (e.g., aneurysms having a neck diameter from 3 mm to 5 mm) and/or shapes (e.g., aneurysm necks having a non-circular shape, such as oblong or peanut-shaped), as well as challenging aneurysm types such as wide-necked aneurysms (e.g., aneurysms having a neck diameter greater than 4 mm and/or a dome-to-neck ratio less than 2). Additionally, the spiral struts can brace the anchor structure radially outward against the wall of the aneurysm near the neck, thus reducing the likelihood of the device becoming dislodged and/or prolapsing into the parent vessel. Moreover, the addition of protrusions extending away from the spiral struts within the common plane can increase the coverage area over the neck of the aneurysm, thereby increasing the occlusive effect of the implanted device. Once deployed, the devices herein can be contained partially or entirely within the aneurysm sac with little or no protrusion into the parent vessel, thus reducing the likelihood of clot formation and/or avoiding the need for concomitant DAPT.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

As used herein, the terms "vertical," "lateral," "upper," and "lower" can refer to relative directions or positions of features of the embodiments disclosed herein in view of the orientation shown in the Figures. For example, "upper" or "uppermost" can refer to a feature positioned closer to the top of a page than another feature. These terms, however, should be construed broadly to include embodiments having other orientations, such as inverted or inclined orientations where top/bottom, over/under, above/below, up/down, and left/right can be interchanged depending on the orientation.

Figure 1B:
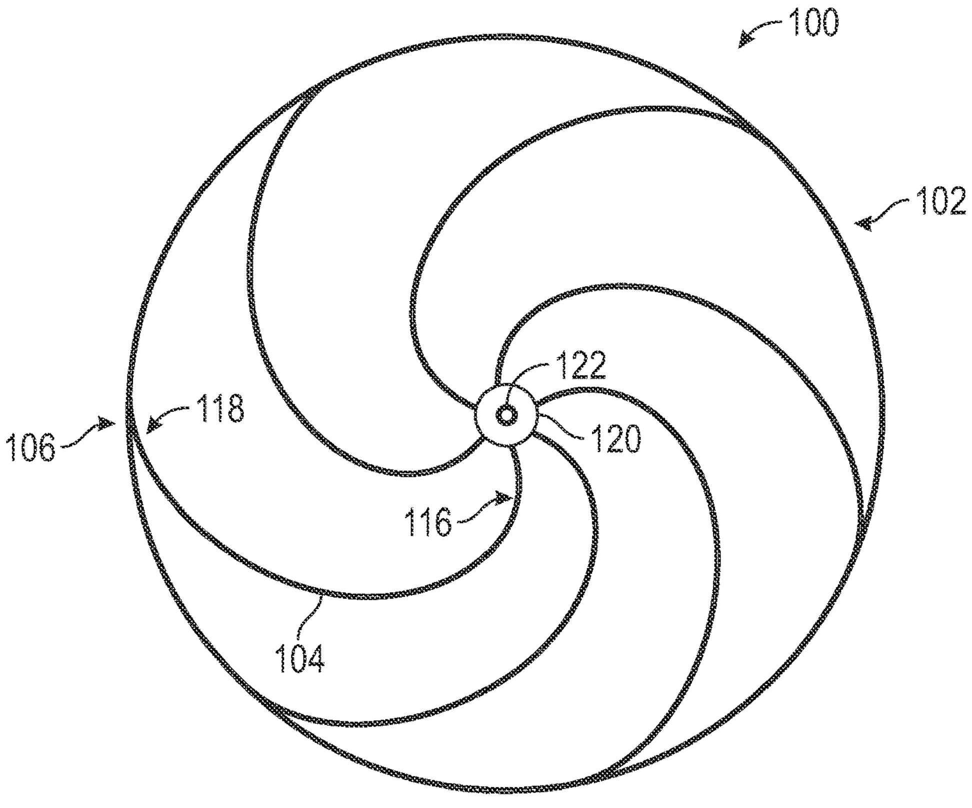
FIG. 1B is a bottom view of the occlusive device of FIG. 1A.

FIGS. 1A and 1B are perspective and bottom views, respectively, of an occlusive device 100 ("device 100") for treating an aneurysm, in accordance with embodiments of the present technology. Referring first to FIG. 1A, the device 100 is configured to be deployed within an aneurysm sac. As described further below, the device 100 can be positioned over the neck of the aneurysm to prevent an embolization element (e.g., a coil) from prolapsing from the aneurysm sac into the parent vessel. The device 100 can also reduce or prevent blood flow from the parent vessel into the aneurysm sac, and/or provide a scaffold for endothelial cell attachment. The growth and development of an endothelial layer over the aneurysm neck can wall off the aneurysm from the parent vessel and allow flow dynamics to equilibrate at the defect. Upon endothelialization, the fluid pressure can be evenly distributed along the parent vessel in a manner that prevents recanalization at the defect post-treatment. Moreover, blood from within the parent vessel no longer has access to the walled-off defect once the endothelialization process is complete. Accordingly, the device 100 can facilitate healing of the defect and/or prevent recanalization.

The device 100 includes an anchor structure 102 coupled to a plurality of curved struts 104. The anchor structure 102 is configured to anchor the device 100 at or near the neck of the aneurysm, while the curved struts 104 are configured to retain an embolization element within the device 100, as described in further detail below. The anchor structure 102 includes a proximal end portion 106, a distal end portion 108, and a mesh surface 110 extending between the proximal end portion 106 and distal end portion 108. In some embodiments, the proximal end portion 106 and distal end portion 108 each have a respective opening, such that the anchor structure 102 includes a lumen extending between the proximal end portion 106 and distal end portion 108, and surrounded by the mesh surface 110. The length L of the anchor structure 102 (e.g., as measured from the proximal end portion 106 to the distal end portion 108 when the device 100 is fully expanded) can be no more than 4 mm, 3.5 mm, 3 mm, 2.5 mm, 2 mm, 1.5 mm, or 1 mm. The width W or diameter of the anchor structure 102 (e.g., as measured when the device 100 is fully expanded) can be at least 5 mm, 4.5 mm, 4 mm, 3.5 mm, 3 mm, 2.5 mm, 2 mm, 1.5 mm, or 1 mm. Although FIG. 1B depicts the anchor structure 102 as having a circular cross-sectional shape, in other embodiments, the anchor structure 102 can have a different shape (e.g., oval, triangular, square, pentagonal, hexagonal, heptagonal, octagonal).

In the embodiment of FIGS. 1A and 1B, the anchor structure 102 is a stent or stent-type structure, with the mesh surface 110 including a plurality of elongate members 112 (e.g., struts) that are interconnected to form cells 114. The geometry of the cells 114 and elongate members 114 can be configured in many different ways. In the illustrated embodiment, for example, the cells 114 are six-sided (e.g., hexagonal) closed cells. The distal apices 115 of the cells 114 can be rounded to reduce the likelihood of tissue perforation when deploying the device 100 in the aneurysm. In other embodiments, however, some or all of the cells 114 can have a different number of sides (e.g., three, four, five, or more), shape (e.g., triangular, square, rectangular, diamond, trapezoidal, parallelogram, pentagonal), be open rather than closed, have sharp distal apices 115 rather than rounded distal apices 115, and/or any other suitable configuration. Additionally, although the anchor structure 102 in FIG. 1A includes a single circumferential ring of cells 114, in other embodiments, the anchor structure 102 can include multiple circumferential rings of cells 114 arranged longitudinally between the proximal end portion 106 and the distal end portion 108. Moreover, although the elongate members 112 are shown as being linear, in other embodiments, some or all of the elongate members 112 can be curved (e.g., sinusoidal, serpentine), curvilinear, or any other suitable geometry. The size (e.g., length, width, height, perimeter, cell area) of the cells 114 can also be varied as desired.

The curved struts 104 are connected to the proximal end portion 106 of the anchor structure 102. As best seen in FIG. 1B, the curved struts 104 are disposed over the opening of the proximal end portion 106 of the anchor structure 102 in a spiral and/or helical configuration. Accordingly, the curved struts 104 may also be referred to interchangeably herein as "spiral struts" or "helical struts." The curvature of the curved struts 104 can be oriented in the same direction, such as in a clockwise direction or a counterclockwise direction, to form the spiral and/or helical configuration. For instance, each strut 104 can curve such that an intermediate portion between an inner end portion coupled to the hub 120 and an outer end portion coupled to the anchor structure 102 is deflected in a circumferential direction. Moreover, each strut 104 can have its intermediate portion deflected in the same circumferential direction (e.g., clockwise or counterclockwise) such that the plurality of curved struts together assume a spiral or helical configuration.

In some embodiments, each curved strut 104 includes a first end region 116 (e.g., a proximal end region) coupled to a hub 120 and a second end region 118 (e.g., a distal end region) coupled to the proximal end portion 106 of the anchor structure 102. The second end region 118 of each curved strut 104 can be coupled to a proximal apex 119 of a respective cell 114 of the anchor structure 102. In other embodiments, however, the second end region 118 can be coupled to a different portion of the cell 114, such as to a lateral edge of the cell 114. The hub 120 can be generally aligned with the center of the opening of the proximal end portion 106, and the second end regions 118 of the curved struts 104 can be spaced apart along the peripheral edge of the proximal end portion 106, such the separation distance between the curved struts 104 increases as the curved struts 104 radiate outward from the hub 120. The spacing between the curved struts 104 can be sufficiently large to permit an embolization element delivery device (e.g., a microcatheter or other elongate shaft) to pass through, but sufficiently small such that the embolization element does not prolapse into the parent vessel. In some embodiments, the average and/or maximum distance between neighboring curved struts 104 is no more than 2.5 mm, 2.25 mm, 2 mm, 1.75 mm, 1.5 mm, 1.25 mm, 1 mm, 0.75 mm, or 0.5 mm.

The configuration of the curved struts 104 can be varied in many different ways. For example, although FIG. 1B depicts the device 100 as including six curved struts 104, in other embodiments, the device 100 can include a different number of curved struts 104 (e.g., 2, 3, 4, 5, 7, 8, 9, 10, 20, or more). As another example, although each curved strut 104 is shown as having the same geometry (e.g., length, width, thickness, curvature), in other embodiments, some or all of the curved struts 104 can have different geometries. In a further example, although FIG. 1B depicts the curved struts 104 as being evenly spaced, in other embodiments the spacing can be varied as desired (e.g., the struts 104 can be clustered into one or more groups that are separated by larger gaps).

Referring to FIGS. 1A and 1B together, when the device 100 is deployed within the aneurysm, the anchor structure 102 is configured to self-expand such that the mesh surface 110 engages the inner wall of the aneurysm sac and applies a radially outward bracing force to anchor the device 100 at the desired location. The curved struts 104 also self-expand together with the anchor structure 102 to bridge the aneurysm neck. Optionally, the expansion of the curved struts 104 can also exert forces in a radially outward direction to further enhance engagement of the anchor structure 102 with the aneurysm wall. In yet another option, the expansion of the curved struts 104 is at least partially caused by the expansion of the anchor structure 102. In some embodiments, the spiral and/or helical configuration of the curved struts 104 enables the curved struts 104 to expand to a wider range of neck diameters while lying substantially within a single plane. Stated differently, the height H (FIG. 1A) of each curved strut 104 in its expanded configuration (e.g., as measured vertically from the first end region 116 to the second end region 118) can be no more than 25%, 20%, 15%, 10%, 5%, 2%, 1%, or 0.1% of the width W of the anchor structure 102. For example, the height H in the expanded configuration can be no more than 1.25 mm, 1 mm, 0.5 mm, 0.25 mm, or 0.1 mm. Accordingly, when deployed, the curved struts 104 can be contained partially or entirely within the aneurysm sac with little or no protrusion into the parent vessel, even if the device 100 is not fully expanded to its maximum diameter. In contrast, other strut designs (e.g., straight struts) may not be substantially planar if the device is not fully expanded, and thus may extend significantly out of the aneurysm and into the parent vessel after deployment.

In the illustrated embodiment, the hub 120 is a collar, band, ring, etc., that crimps or otherwise holds the first end regions 116 of the curved struts 104 together. Alternatively, the hub 120 can simply be the location where the first end regions 116 are connected to each other (e.g., via welding, bonding, adhesives, or may comprise a contiguous part of the flat sheet of material from which the device is laser-cut or etched, preferably forming a ring), rather than a separate component. As best seen in FIG. 1A, the hub 120 can be coupled to a detachment element 122 configured to releasably couple to a pusher member (not shown). The pusher member can be an elongate rod, shaft, wire, etc., that is configured to push the device 100 through a distal end of a delivery catheter to deploy the device 100 within the aneurysm, as described further below. Optionally, the pusher member can also be used to pull the device 100 partially or fully back into the delivery catheter, e.g., for repositioning purposes. The detachment element 122 can utilize any suitable detachment (releasable coupling) technique known to those of skill in the art, such as electrolytic detachment, mechanical detachment, thermal detachment, electromagnetic detachment, or combinations thereof. An example of a detachment element for suitable use with the present technology is the Axium™ or Axium™ Prime Detachable Coil System (Medtronic).

Optionally, the device 100 can include one or more radiopaque portions so the physician can visualize the location and configuration of the device 100 during deployment in the aneurysm. For example, radiopaque markers (not shown) can be incorporated into the device 100 at or near the distal apices 115, at or near the proximal apices 119, at or near the intersections of adjacent cells 114, at or near the second end regions 118 of the curved struts 104, at or near the first end regions 116 of the curved struts 104, and/or on or within the hub 120.

The device 100 can be manufactured in many different ways. For example, the anchor structure 102 and/or curved struts 104 can be formed by laser-cutting of a tube or sheet, etching, metal injection molding, braiding, or any other suitable manufacturing process. In some examples, the device is formed by laser-cutting a flat sheet, which is then heat set in a desired configuration, for example with the anchor structure 102 extending approximately perpendicular upwardly from the plane of the sheet in which the curved struts 104 lie. Optionally, components of device cut from a single flat sheet can be welded or otherwise joined together after or in combination with being heat set into a desired configuration.

In some embodiments, the anchor structure 102 and curved struts 104 are integrally formed as a single unitary component. In other embodiments, the anchor structure 102 and curved struts 104 can be discrete components that are attached to each other, e.g., using welding, adhesives, fasteners, or other suitable techniques. The anchor structure 102 and/or curved struts 104 can be formed of known flexible materials, including shape memory and/or superelastic materials (e.g., Nitinol), cobalt chromium, platinum, stainless steel, other metals or metal alloys, or a combination thereof. Optionally, portions of the anchor structure 102 and/or curved struts 104, or the entirety of the anchor structure 102 and/or curved struts 104, can include one or more coatings or surface treatments, such as coatings or treatments to increase lubricity and/or reduce the delivery force as the device 100 is advanced through the delivery catheter, increase hydrophilicity, and/or enhance blood compatibility and reduce thrombogenic surface activity. For example, an anti-thrombogenic coating or treatment can be applied to the curved struts 104, hub 120, and/or detachment element 122.

In some embodiments, the device 100 is configured to transform between a first, low-profile configuration suitable for delivery via an elongate shaft (e.g., a delivery catheter) and a second, expanded configuration suitable for bridging the neck of an aneurysm (e.g., the configuration illustrated in FIGS. 1A and 1B). In such embodiments, the anchor structure 102 and/or curved struts 104 can be shape set (e.g., heat set) in the expanded configuration, such that the device 100 self-expands into the expanded configuration when deployed into the aneurysm. For example, the anchor structure 102 and curved struts 104 can both be shape set into a fully expanded configuration in which the anchor structure 102 is opened to its maximum width and/or diameter, and/or the distance spanned by the curved struts 104 is substantially equal to the maximum width and/or diameter of the anchor structure 102. In such embodiments, the self-expansion of the curved struts 104 can actively push the anchor structure 102 radially outward to further enhance engagement with the aneurysm wall. Alternatively, the anchor structure 102 can be shape set in the fully expanded configuration, while the curved struts 104 are shape set into a partially expanded configuration in which the distance spanned by the curved struts 104 is less than the maximum width and/or diameter of the anchor structure 102. In such embodiments, the curved struts 104 can be "passive" elements that are pulled open by the self-expansion of the anchor structure 102.

FIGS. 2A-2G illustrate a method of treating an aneurysm with an occlusive device, in accordance with embodiments of the present technology. Although the illustrated embodiment is shown and described in terms of the device 100 of FIGS. 1A and 1B, the method can be applied to any embodiment of the occlusive devices described herein (e.g., the devices 300, 400 of FIGS. 3A-4B).

Figure 2A:
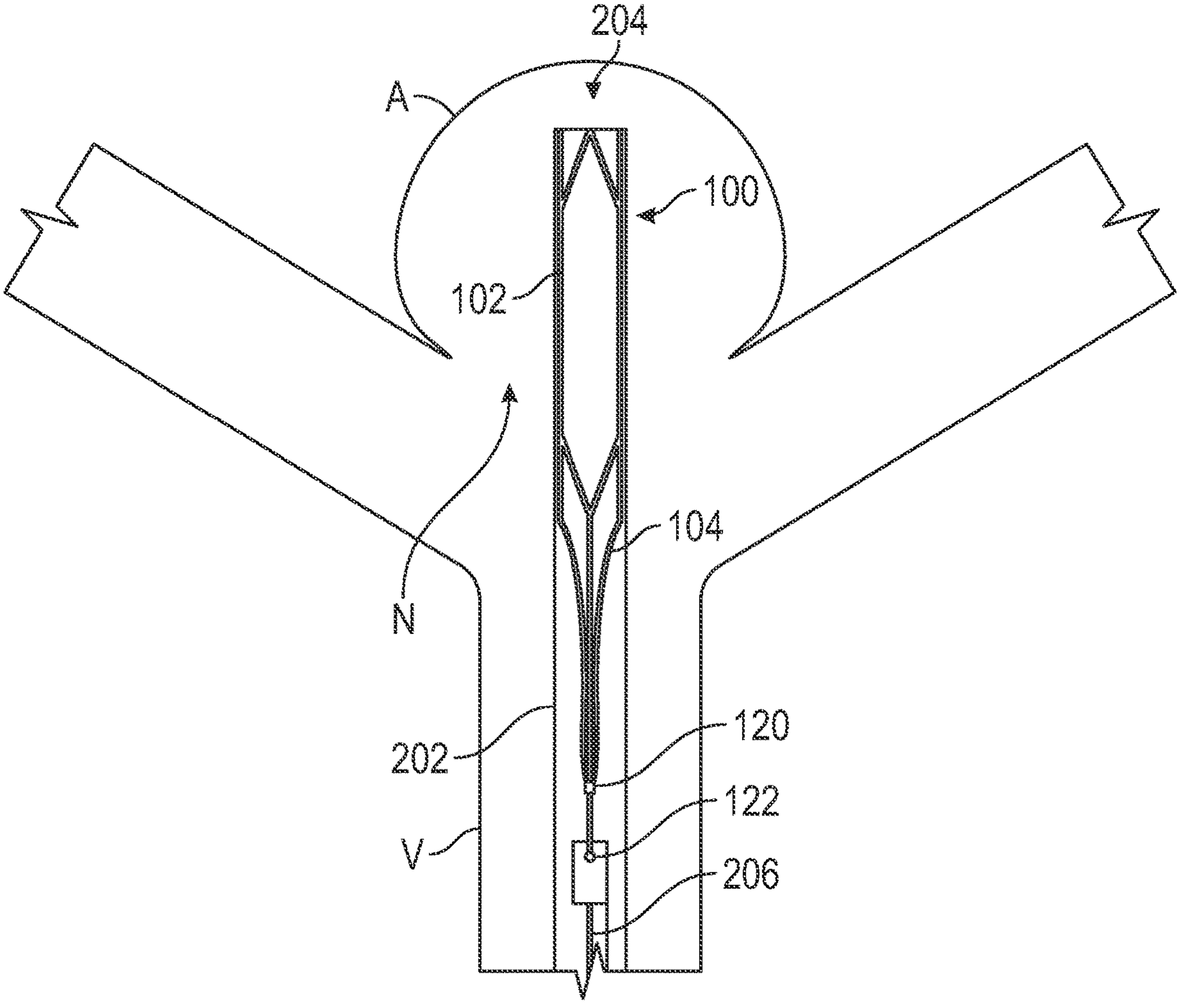
FIG. 2A is a partially schematic side view of an occlusive device being introduced into an aneurysm, in accordance with embodiments of the present technology.

Referring first to FIG. 2A, the device 100 can be loaded within a first elongate shaft 202 (e.g., a delivery catheter such as a microcatheter) in a low-profile configuration. When in the low-profile configuration, the anchor structure 102 and curved struts 104 of the device 100 can be compressed, flattened, or otherwise compacted in a generally linear configuration to conform to the interior lumen of the first elongate shaft 202. In the illustrated embodiment, for example, the curved struts 104 are constrained in a generally straightened state and extend proximally away from the anchor structure 102. The distance between the most proximal portion of the curved struts 104 and the most proximal portion of the anchor structure 102 can be at least 1 mm, 2 mm, 3 mm, 4 mm, or 5 mm. The device 100 can then be intravascularly delivered to a location within a blood vessel V adjacent a target aneurysm A via the first elongate shaft 202. As shown in FIG. 2A, a distal tip 204 of the first elongate shaft 202 can be advanced through the neck N of the aneurysm A and into an interior cavity of the aneurysm A.

Figure 2B:
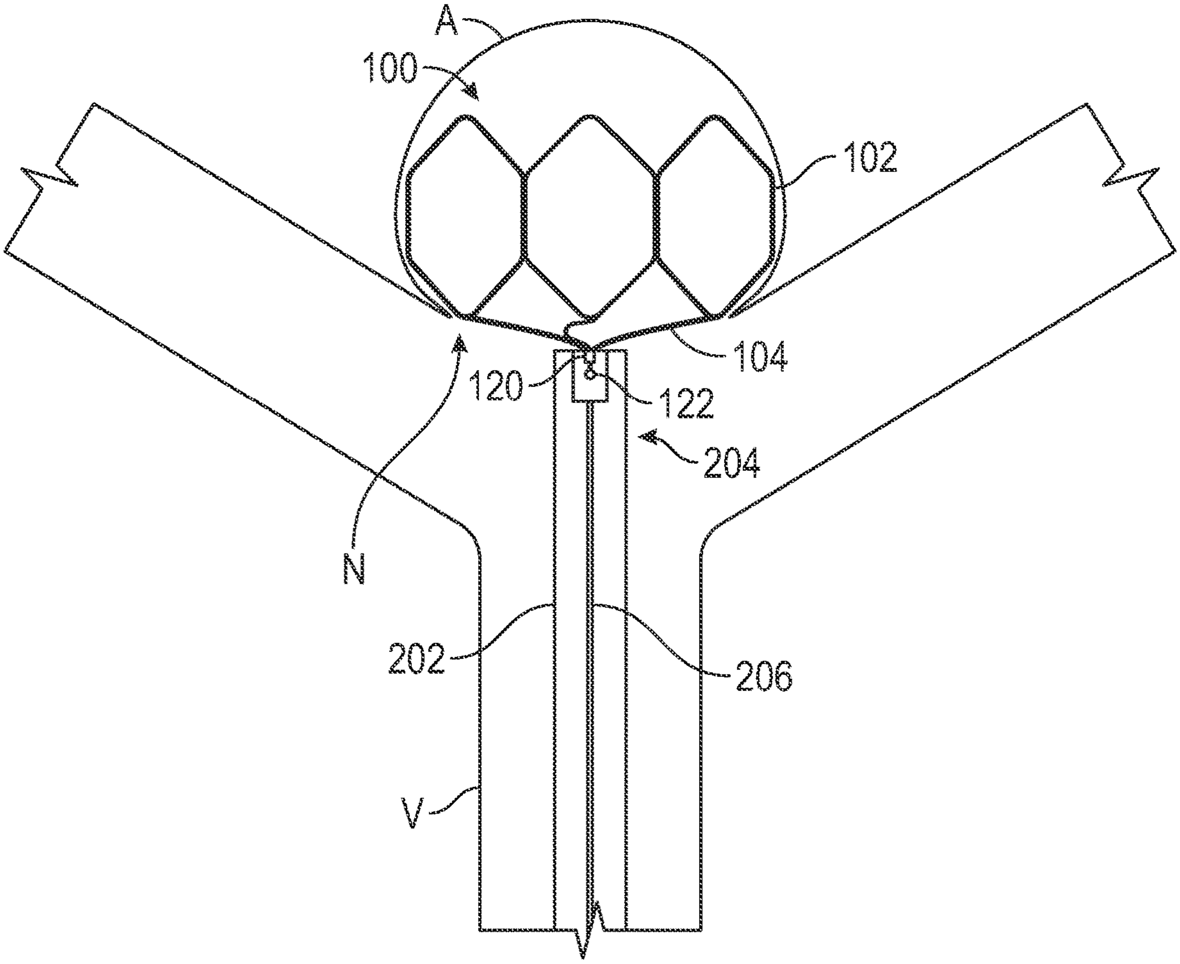
FIG. 2B is a partially schematic side view of the occlusive device of FIG. 2A being deployed in the aneurysm.

Referring next to FIG. 2B, the device 100 can then be deployed by pushing the device 100 distally through the opening in the distal tip 204 of the first elongate shaft 202 and into the aneurysm cavity, e.g., using a pusher member 206 coupled to the detachment element 122 and/or hub 120. As the anchor structure 102 and curved struts 104 of the device 100 exit the first elongate shaft 202, these components can self-expand from the low-profile configuration into the expanded configuration.

Figure 2C:
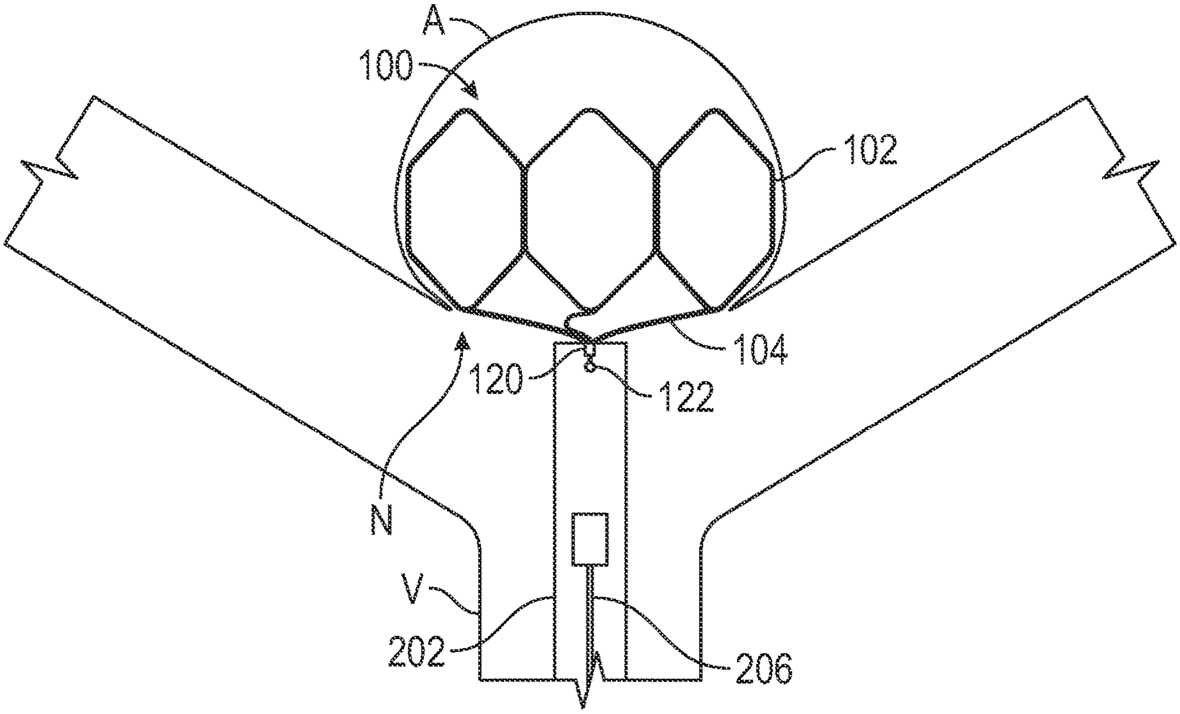
FIG. 2C is a partially schematic side view of the occlusive device of FIG. 2B after detachment from a pusher member.

Referring next to FIG. 2C, once the device 100 is deployed, the detachment element 122 and/or hub 120 can be detached from the pusher member 206. The pusher member 206 and first elongate shaft 202 can then be withdrawn from the aneurysm A.

Figure 2D:
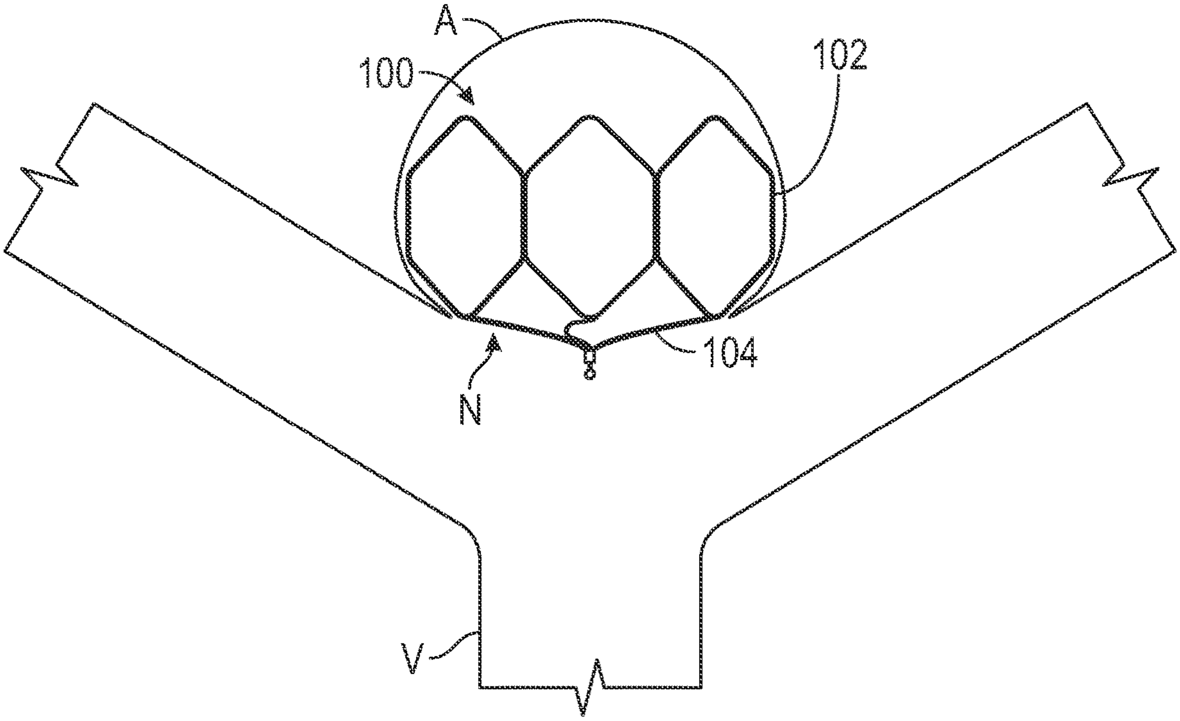
FIG. 2D is a partially schematic side view of the occlusive device of FIG. 2C after deployment.
Figure 2E:
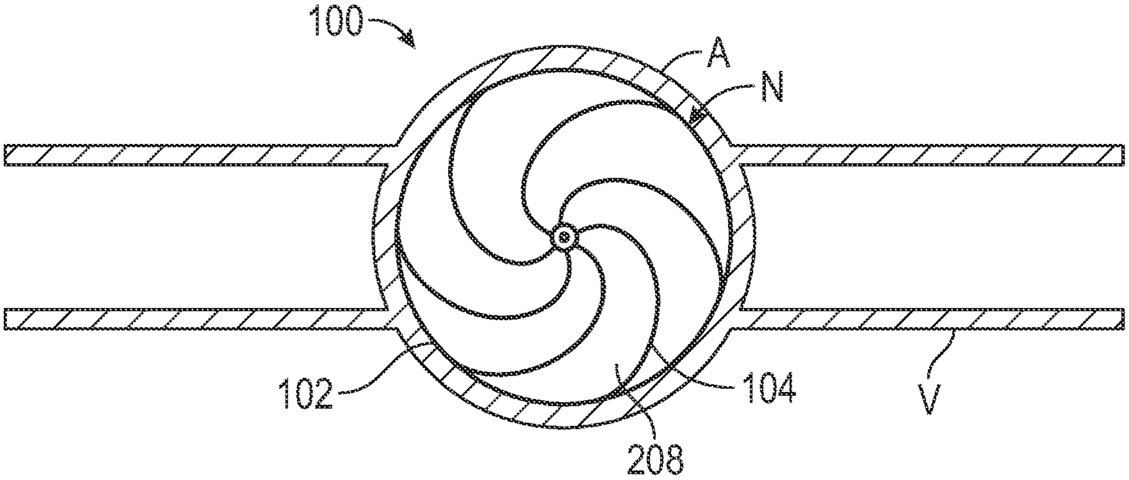
FIG. 2E is a partially schematic bottom view of the occlusive device of FIG. 2D.

Referring next to FIG. 2D, when the device 100 is deployed, the curved struts 104 are arranged in a spiral and/or helical configuration bridging the aneurysm neck N, while the anchor structure 102 engages the inner wall of the aneurysm A at or near the neck N. The anchor structure 102 and curved struts 104 can collectively generate a bracing force directly radially outward against the aneurysm wall that prevents the device 100 from being displaced out of the aneurysm A and into the vessel V. As previously described, when in the expanded configuration, the curved struts 104 can lie substantially within a single plane (e.g., the plane of the aneurysm neck N), such that there is little or no protrusion of the curved struts 104 into the vessel V. For example, when expanded, the distance between the most proximal portion of the curved struts 104 and the most proximal portion of the anchor structure 102 can be smaller than the initial distance in the low-profile configuration, such as no more than 1 mm, 0.5 mm, 0.25 mm, or 0.1 mm. This approach can be advantageous for reducing disruptions to blood flow in the vessel V, which may lead to thrombus formation. As best seen in FIG. 2E (showing a bottom view of FIG. 2D), the curved struts 104 can only partially occlude the aneurysm neck N, thus leaving one or more gaps 208 providing a passageway from the vessel V into the aneurysm A.

Figure 2F:
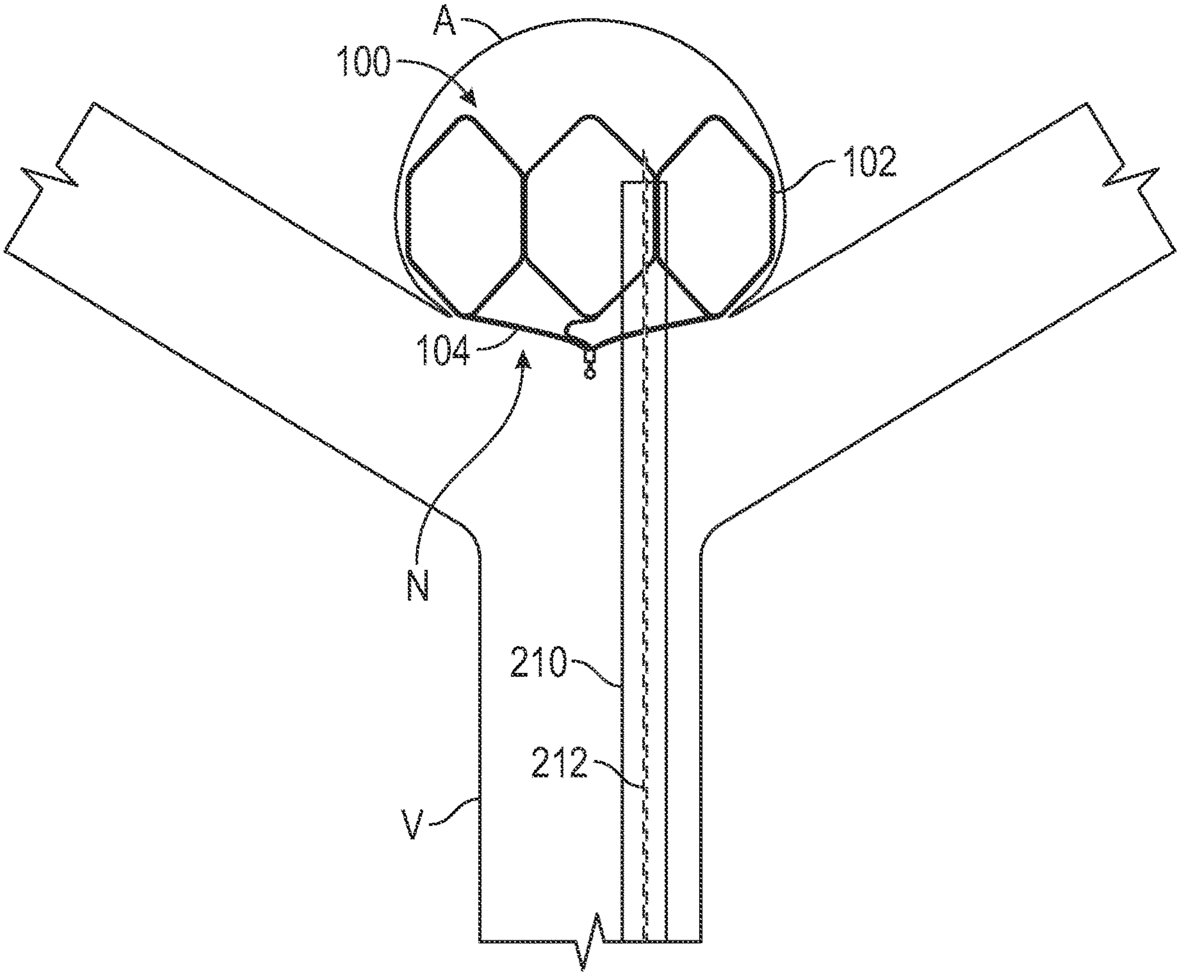
FIG. 2F is a partially schematic side view of an embolization coil being introduced into the aneurysm, together with the occlusive device of FIG. 2D.

Referring next to FIG. 2F, a second elongate shaft 210 (e.g., a second delivery catheter, such as a microcatheter) can subsequently be used to introduce an embolization coil 212, or a plurality of embolization coils, or other embolization element into the aneurysm A. The second elongate shaft 210 can be advanced through one of the gaps 208 (FIG. 2E) between the curved struts 104 and into the interior of the aneurysm A. The coil 212 can then be deployed out of the distal opening of the second elongate shaft 210 and into the aneurysm A. In other embodiments, however, the first elongate shaft 202 can be used to introduce both the device 100 and the coil 212 into the aneurysm A.

Figure 2G:
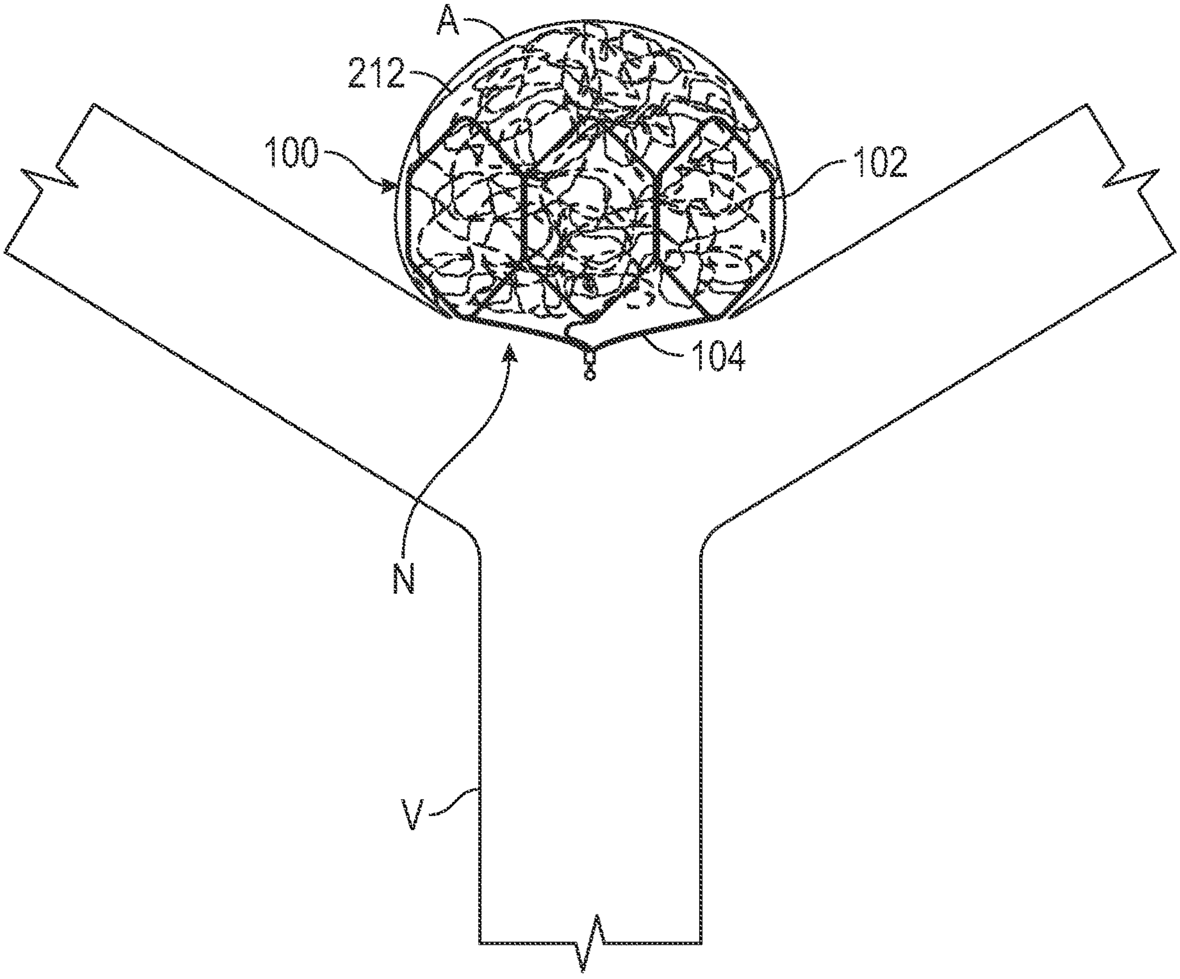
FIG. 2G is a partially schematic side view of the occlusive device and the embolization coil of FIG. 2F after deployment.

Referring next to FIG. 2G, once fully deployed, the coil(s) 212 can fill most or substantially all of the space within the aneurysm A. The coil 212 can be formed of one or more wires wound in a helical fashion about an axis to form an elongate tubular member. The wire(s) forming the coil 212 can be circular, square, or rectangular in cross-section, and can have a cross-sectional dimension (e.g., width, radius) from 0.001 inches to 0.003 inches, or from 0.0015 inches to 0.0025 inches. In some embodiments, the wire(s) forming the coil 212 have a cross-sectional dimension no greater than 0.003 inches, 0.0025 inches, or 0.002 inches. The coil 212 can be circular, square, or rectangular in cross-section, and can have a cross-sectional dimension (e.g., width, radius) from 0.01 inches to 0.02 inches, from 0.012 inches to 0.018 inches, or from 0.014 inches to 0.016 inches. In some embodiments, the coil 212 has a cross-sectional dimension that is no greater than 0.0145 inches or 0.0140 inches.

The coil 212 can have a length from 2 cm to 30 cm, from 3 cm to 25 cm, or from 4 cm to 20 cm. In some embodiments, the length of the coil 212 depends on the size of the aneurysm being treated. For example: for an aneurysm 4 mm in diameter or less, the coil 212 can have a length of about 6 cm; for an aneurysm 5 mm in diameter or less, the coil 212 can have a length of about 8 cm; for an aneurysm 6 mm in diameter or less, the coil 212 can have a length of about 15 cm; for an aneurysm 7 mm in diameter or less, the coil 212 can have a length of about 15 cm; for an aneurysm 8 mm in diameter or less, the coil 212 can have a length of about 20 cm; and, for an aneurysm 9 mm in diameter or less, the coil 212 can have a length of about 20 cm.

The coil 212 can be made from metals, alloys, polymers, shape memory materials (e.g., Nitinol), platinum, rhodium, palladium, tungsten, gold, silver, cobalt-chromium, platinum tungsten, and/or various alloys of these materials. In some embodiments, the coil 212 is heat set to form a tertiary structure (e.g., a pre-determined three-dimensional structure) when in a deployed state. For example, the coil 212 can have a preset tertiary structure that biases the coil into a bundled or more globular state that facilitates positioning of the coil 212 between the deployed device 100 and the aneurysm wall. In other embodiments, however, the coil 212 may not have a tertiary structure.

As previously mentioned, embolic coils such as the coil 212 can be very effective at filling space within the aneurysm cavity. However, there is a risk that the coil 212 may prolapse through the neck N of the aneurysm A into the vessel V, particularly if the aneurysm A is a wide-necked aneurysm. The device 100 can address this challenge via the curved struts 104 that are positioned over the aneurysm neck N to support the coil 212 and prevent the coil 212 from protruding into the neck, while the anchor structure 102 braces against the aneurysm wall to resist the outward pressure toward the vessel V exerted by the packed coil 212 so the device 100 does not bulge into the vessel V.

The methods of the present technology can be performed under fluoroscopy such that the radiopaque portions of the device 100 can be visualized by the physician to ensure proper neck coverage. If the device 100 is not positioned properly, the physician can withdraw the device 100 into the first elongate shaft 202, reposition, and deploy again. Additionally, in embodiments where the coil 212 is radiopaque, the physician can use fluoroscopy to confirm that the coil 212 does not protrude from the neck N of the aneurysm A after deployment.

FIGS. 3A-8C illustrate additional examples of occlusive devices 300, 400 for treating an aneurysm, in accordance with embodiments of the present technology. The devices 300, 400, 500, 700, and 800 of FIGS. 3A-8C can be generally similar to the device 100 of FIGS. 1A and 1B. Accordingly, like numbers (e.g., curved strut 104 versus curved strut 304) are used to identify similar or identical structures, and discussion of the devices 300, 400, 500, 700, and 800 of FIGS. 3A-8C will be limited to those features that differ from the device 100 of FIGS. 1A and 1B. Additionally, any of the features of the devices 100, 300, 400, 500, 700, and 800 can be combined with each other.

Figure 3A:
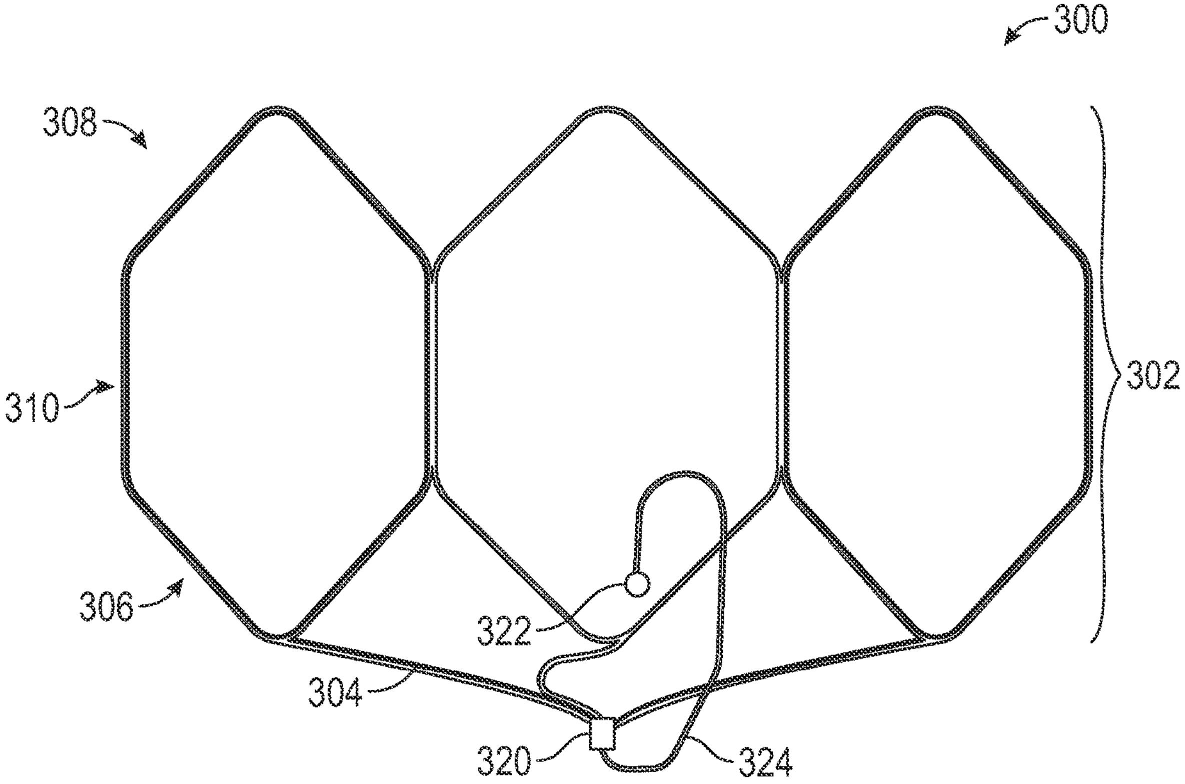
FIG. 3A is a side view of an occlusive device with a connector in an expanded configuration, in accordance with embodiments of the present technology.

Referring to FIG. 3A, the device 300 is generally similar to the device 100 of FIGS. 1A and 1B, except that the device 300 includes a connector 324 (e.g., a filament, wire, shaft, strut, or other elongate member) coupling the hub 320 to the detachment element 322. The connector 324 can have any suitable length, such as a length of at least 1 mm, 2 mm, 3 mm, 4mm, 5 mm, 10 mm, or more. The connector 324 can be made of a flexible material having shape memory and/or superelastic properties (e.g., Nitinol), such that the connector 324 can be shape set to transform from a first (e.g., constrained) state for delivery to a second (e.g., unconstrained) state for deployment in an aneurysm.

Figure 3B:
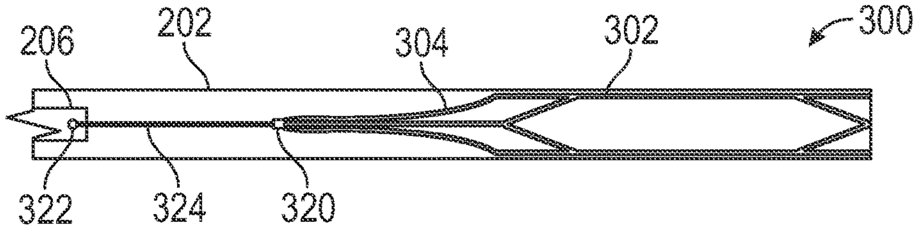
FIG. 3B is a side view of the occlusive device of FIG. 3A in a low-profile configuration.

FIG. 3B illustrates the device 300 in a low-profile configuration within the first elongate shaft 202. In the illustrated embodiment, when the device 300 is in the low-profile configuration, the connector 324 is in the first state and has a generally straightened shape that extends proximally away from the anchor structure 302 and curved struts 304. Accordingly, the detachment element 322 is accessible by and can be coupled to the pusher member 206.

Referring again to FIG. 3A, when the device 300 is deployed from the first elongate shaft 202 and separated from the pusher member 206 (e.g., in accordance with the techniques described above with respect to FIGS. 2A-2G), the connector 324 is no longer constrained and thus transforms to the second state. In the second state, the connector 324 can be bent and/or curved (e.g., coiled) in a distal direction such that at least a portion of the connector 324 and the detachment element 322 pass through the gaps between the curved struts 304 and are disposed within the lumen of the anchor structure 302 distal to the proximal end portion 306 of the anchor structure 302. Accordingly, when the device 300 is deployed in the aneurysm, the connector 324 and detachment element 322 can be contained partially or entirely within the aneurysm sac, thus avoiding disruptions to blood flow in the parent vessel.

Figure 4A:
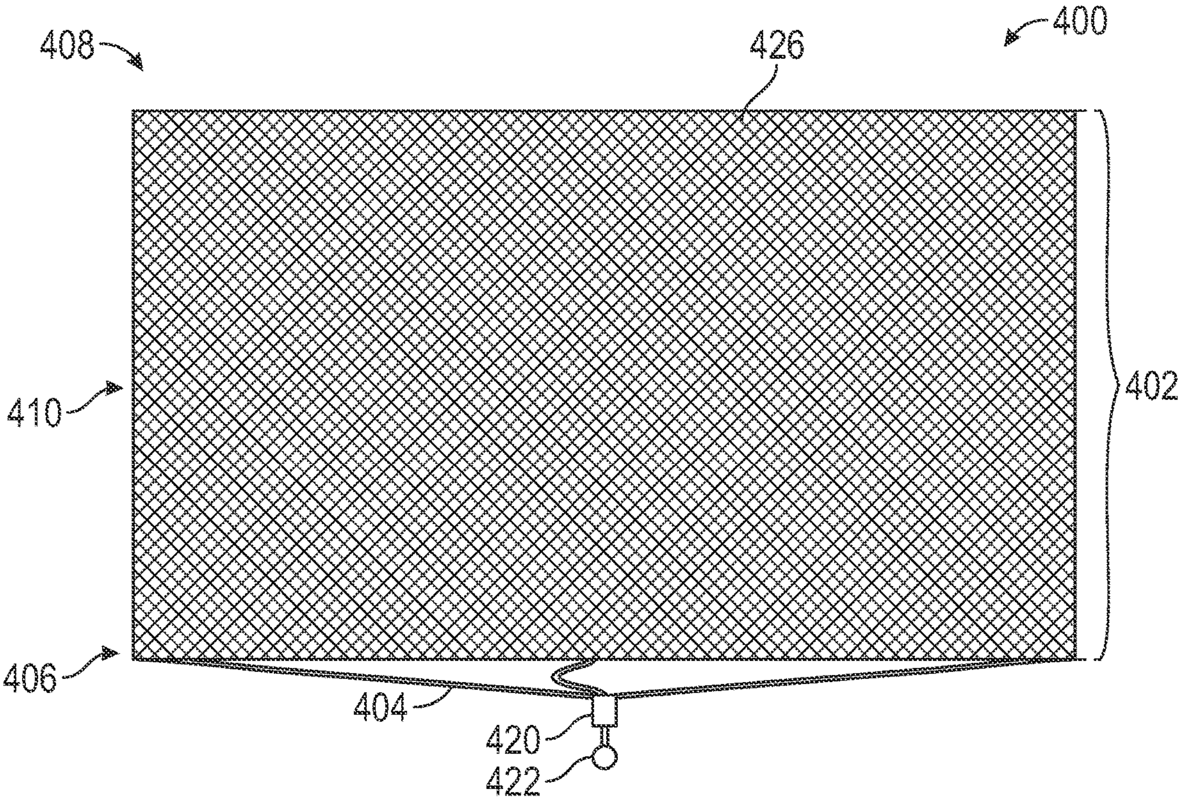
FIG. 4A is a side view of an occlusive device including a braided anchor structure in an expanded configuration, in accordance with embodiments of the present technology.
Figure 4B:
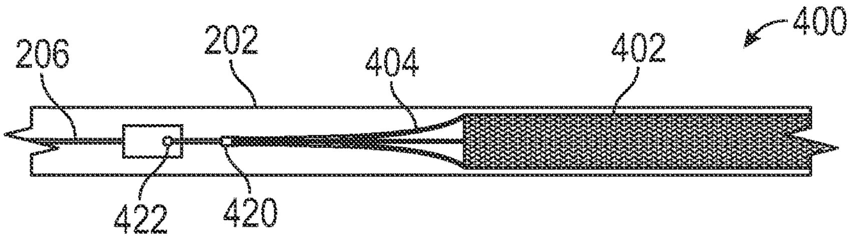
FIG. 4B is a side view of the occlusive device of FIG. 4A in a low-profile configuration.

Referring next to FIG. 4A, the device 400 is generally similar to the device 100 of FIGS. 1A and 1B, except that the anchor structure 402 is a braid formed from a plurality of filaments 426 (e.g., wires). The filaments 426 are braided, woven, or otherwise interconnected to form the mesh surface 410 of the anchor structure 402. The braid can be self-expandable such that the device 400 can transform from a low-profile configuration (FIG. 4B) in which the braid is radially constrained and/or compressed, to an expanded configuration (FIG. 4A) in which the braid is expanded radially outward to engage the aneurysm wall.

In some embodiments, some or all of the filaments 426 (e.g., at least 25%, 50%, 80%, or 100% of the filaments 426) are made of one or more shape memory and/or superelastic materials (e.g., Nitinol). The braid can have, for example, from 32 to 144 filaments 426, such as 64 or 72 filaments 426. Some or all of the filaments 426 can have a diameter from 0.0010 inches to 0.0012 inches, such as a diameter of 0.0010 inches, 0.0011 inches, or 0.0012 inches (at least prior to etching). In some embodiments, some or all of the filaments 426 are drawn-filled tubes ("DFT") having a radiopaque core (e.g., platinum) surrounded by a shape memory alloy and/or superelastic alloy (e.g., Nitinol, cobalt chromium, etc.). Radiopaque markers can alternatively or additionally be incorporated into other portions of the device 400, e.g., at or near the distal end portion 408, proximal end portion 406, curved struts 404, hub 420, etc. All or a portion of the length of some or all of the filaments 426 can have one or more coatings or surface treatments. For example, some or all of the filaments 426 can have a lubricious coating or treatment that reduces the delivery force as the device 400 is advanced through the delivery catheter. In some embodiments, the coating is relatively hydrophilic, such as a phosphorocholine compound. Additionally or alternatively, some or all of the filaments 426 can have a coating or treatment (the same as the lubricious coating, or a different coating) that enhances blood compatibility and reduces the thrombogenic surface activity of the braid. Optionally, at least a portion of the filaments 426 can be made of other suitable materials.

In some embodiments, the anchor structure 402 and curved struts 404 are integrally formed as a single unitary component. For example, the curved struts 404 can be formed from the same filaments 426 used to form the braid of the anchor structure 402. In such embodiments, each curved strut 404 can be made from one or more filaments 426 that are bundled, twisted, braided, or otherwise assembled into a single elongate component. Alternatively, the anchor structure 402 and curved struts 404 can be discrete components that are attached to each other, e.g., using welding, adhesives, fasteners, or other suitable techniques. In such embodiments, the curved struts 404 can be formed of known flexible materials, including shape memory and/or superelastic materials (e.g., Nitinol), cobalt chromium, platinum, stainless steel, other metals or metal alloys, or a combination thereof, and can be manufactured by laser-cutting, etching, metal injection molding, braiding, etc.

FIGS. 5A-8C illustrate additional examples of occlusives devices 500, 700, and 800 for treating an aneurysm in accordance with embodiments of the present technology. The devices 500, 700, and 800 can be generally similar to the devices 100, 300, and 400 described previously, except that the devices 500, 700, and 800 can additionally include protrusions extending away from the spiral struts. In various embodiments, these protrusions can increase the surface coverage area of the expanded device across the neck of the aneurysm. The anchor structures of these devices 500, 700, and 800 can also assume a different configuration as described in more detail below.

Figure 5A:
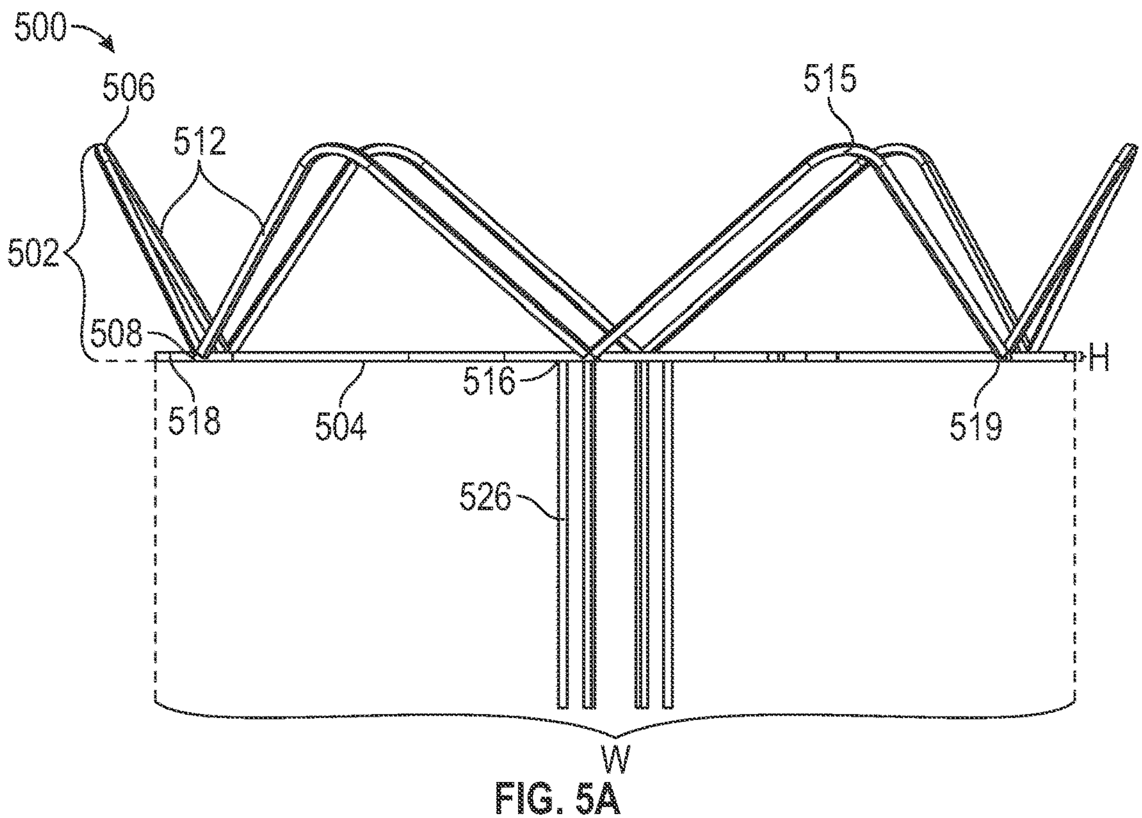
FIG. 5A is a side view of an occlusive device in an expanded configuration, in accordance with embodiments of the present technology.
Figure 5B:
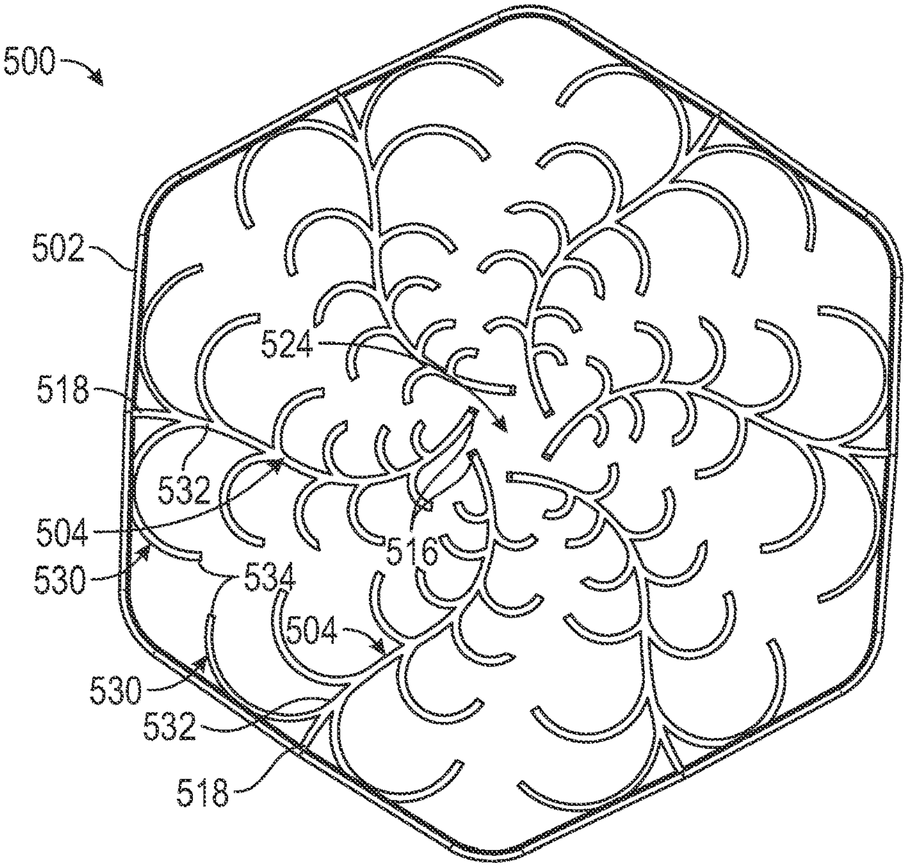
FIG. 5B is a top view of the occlusive device of FIG. 5A.
Figure 5C:
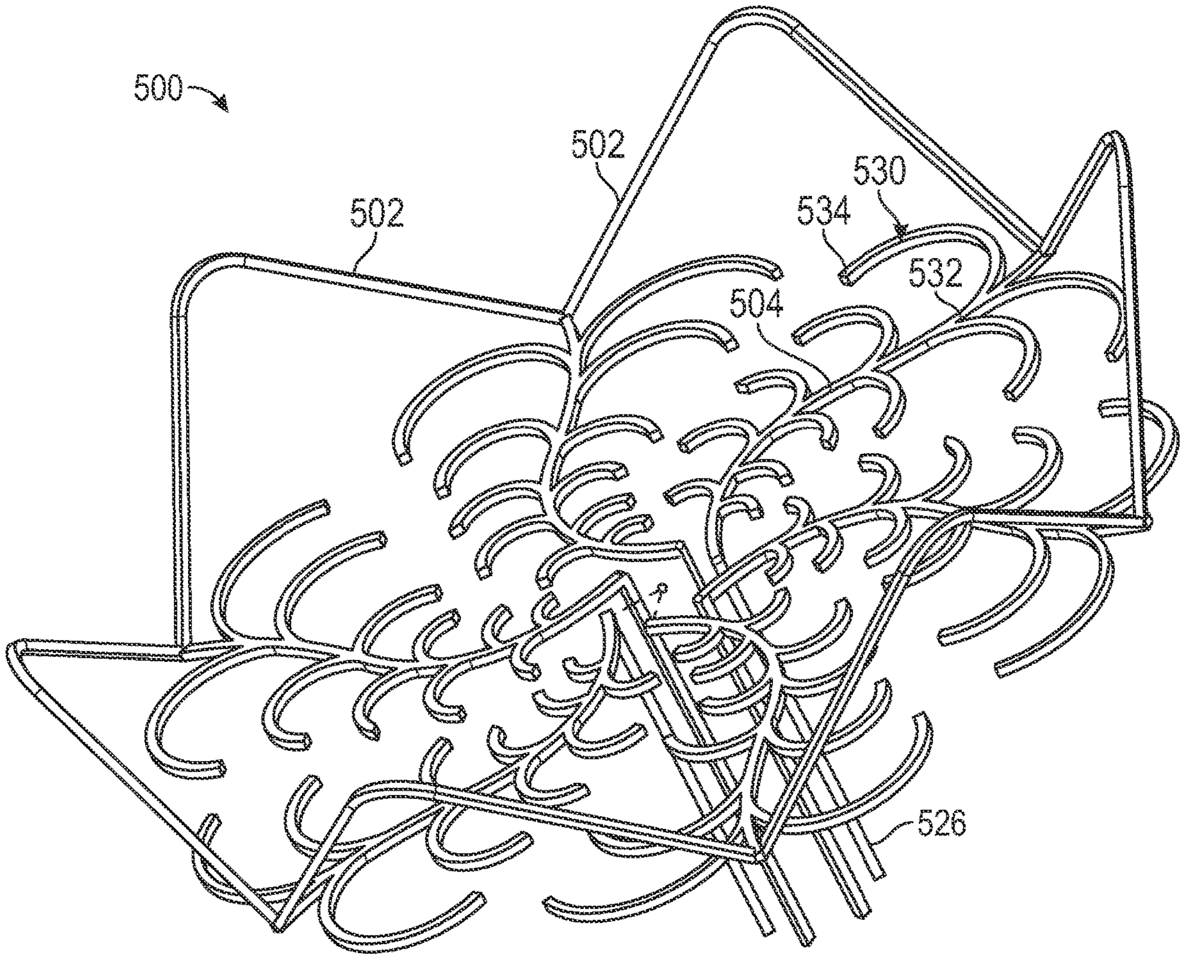
FIG. 5C is an upper perspective view of the occlusive device of FIGS. 5A and 5B.

FIGS. 5A-5C illustrate side, top, and perspective views, respectively, of an occlusive device 500 in its expanded configuration. The device 500 is generally similar to the device 100 of FIGS. 1A and 1B, except that the device 500 includes an anchor structure 502 having a reduced height compared to the device 100 of FIG. 1A and 1B. As illustrated, the anchor structure 502 includes undulating struts 512 in a zig-zag configuration that extend circumferentially around the central opening of the device 500. These undulating struts 512 define distal apices 515 at the first end region 516 of the anchor structure 512 and proximal apices 519 at the second end region 518 of the anchor structure 502. The relatively lower profile aspect of the anchor structure 502 can facilitate placement of the occlusive device 500 in a wide range of aneurysms, while maintaining engagement with the aneurysm wall to secure the device 500 in place. This lower profile aspect can also reduce the diameter of the device while in the collapsed configuration, and therefore improve deliverability of the occlusive device 500, particularly to distal cerebral vessels.

In the illustrated embodiment, the curved struts 504 each have a first end region 516 disposed adjacent a central aperture 524 and a second end region 518 coupled to the anchor structure 502. At the first end region 516, each curved strut 516 abuts a proximal extension 526 that extends proximally away from the plane defined by the curved struts 504. As best seen in FIG. 5C, a plurality of such proximal extensions 526 extend proximally away from the common plane and are arranged substantially parallel to one another. In operation, these proximal extensions 526 can be joined together by or otherwise coupled to a hub (e.g., hub 120 of FIG. 1A). As described previously herein, the hub (or other connection mechanism) can be used to join the occlusive device 500 to a delivery system and/or detachment mechanism for intravascular delivery to the treatment site.

In some embodiments, the central aperture 524 can be defined by a partially or fully continuous circumferential ring. For instance, the first end regions 516 of the curved struts 504 may connect to the ring defining the central aperture 524. The proximal extensions 526 may extend proximally away from the ring, or may be omitted entirely. In some implementations, the ring defining the central aperture 524 can facilitate releasable coupling of the occlusive device 500 to a delivery element (e.g., a pusher member). For instance, an elongate member such as a wire may extend through the central aperture 524 and have a distal anchor disposed distal to the central aperture 524 to secure the wire in place. A proximal portion of the wire can be coupled to or form a part of an elongate delivery member (e.g., a pushwire, hypotube, etc.). To detach the occlusive device, the wire itself can be severed via electrolytic detachment or other mechanism. Additionally or alternatively, the elongate delivery member can be separated from the wire (which is secured to the occlusive device 500) via a mechanical engagement mechanism. Similar releasable engagement techniques can be used for any of the occlusive devices described herein.

As best seen in FIGS. 5B and 5C, a plurality of protrusions 530 extend away from each of the curved struts 504. Each protrusion 530 can include a first end region 532 coupled to one of the curved struts 504 and a second end region 534 that is free (i.e., not connected to another strut or protrusion). In the expanded configuration, the protrusions 530 can be arranged to lie substantially in the same plane as the curved struts 504. Stated differently, when the device 500 is in its expanded configuration, a height H of each curved strut 504 and each protrusion 530 (i.e., a height dimension along the proximal-distal axis) can be no more than 10%, 5%, 2%, 1%, or 0.1% of the width W of the anchor structure 502.

In some examples, some or all of the protrusions 530 that extend away from one of the curved struts 504 can have a second end region 536 that is attached to the anchor structure 502 and/or to another curved strut 504. In such configurations, the protrusion 530 assumes the form of a "branching" of the curved strut 504 in the radially outward direction. Among examples, such branching configurations may reduce the resheathing force needed to collapse the occlusive device 500 from the expanded configuration into a constrained configuration for placement within a delivery catheter.

The protrusions 530 can assume a variety of different shapes, sizes, and configurations. For instance, the protrusions 530 can have straight, arcuate, curved, semi-circular, or semi-elliptical shapes. Protrusions 530 can also have more complex shapes, such as zig-zag, undulating, serpentine, sinusoidal, etc. In some embodiments, the direction of curvature for some or all of the protrusions 530 can be inward toward the central aperture 524 or alternatively direction of curvature can be in the opposite direction (e.g., curving radially outwardly toward the anchor structure 502).

Figure 6A:
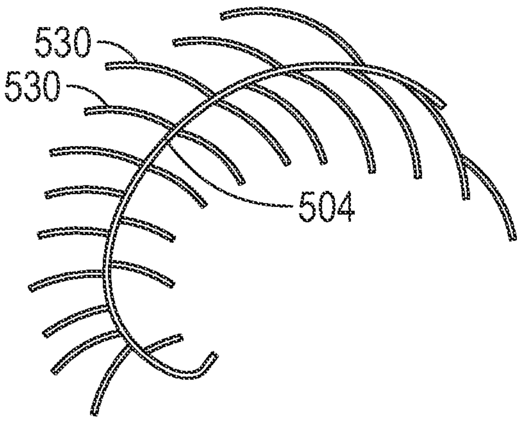
FIGS. 6A-6C illustrate example spiral struts with protrusions extending therefrom in accordance with embodiments of the present technology.
Figure 6B:
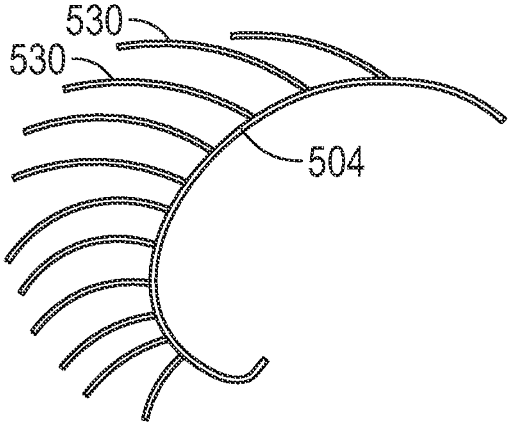
Figure 6C:
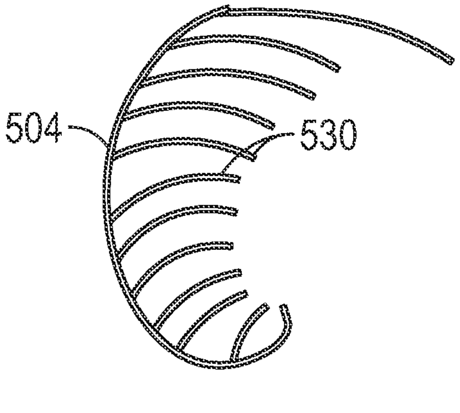

As shown in FIG. 5B, each curved strut 504 can include a plurality of protrusions 530 extending laterally away from the curved strut 504, with the individual protrusions 530 being spaced apart from one another along the length of the curved strut 504. Additionally, protrusions 530 are arranged on opposing sides of the curved strut 504. In various examples, one or more of the struts 504 may have protrusions 530 extending laterally away from both sides of the strut 504 (e.g., as seen in FIGS. 5A-5C and FIG. 6A). Alternatively, one or more curved struts 504 can have protrusions 530 extending away only from one side of the curved strut 504, for example laterally outward from the direction of curvature (as shown in FIG. 6B) or laterally inward toward the direction of curvature (as shown in FIG. 6C). In some examples, a single occlusive device can include curved struts 504 with different configurations of protrusions 530 between them. For instance, a first curved strut 504 may include protrusions 530 extending laterally from both sides of the curved strut 504, while a second curved strut 504 may include protrusions 530 extending away from only one side.

Referring back to FIGS. 5A-5C, in the illustrated example, the length of each protrusion 530 increases from the radially innermost protrusions 530 (i.e., nearest the central aperture 524) to the radially outermost protrusions 530 (i.e., nearest the anchor structure 502). In various embodiments, the lengths of the protrusions 530 may be substantially the same, and/or may vary in other ways (e.g., decreasing in the radially outward direction, or variously increasing and decreasing lengths).

The presence of the protrusions 530 can increase the total material coverage area of the occlusive device over the central opening defined by the ring-shaped anchor structure 502. This increased material coverage area can improve the occlusive effect of the device 500 when implanted within an aneurysm. Depending on the number, configuration, and dimensions of the curved struts 504 and/or the protrusions 530, the material coverage proportion can be selected to achieve a desired coverage ratio. For instance, when the device 500 is viewed from above and in the expanded configuration (as shown in FIG. 5B), the surface area occupied by the curved struts 504 and protrusions 530 over the area defined by the anchor structure 502 can be at least about 5%, 10%, 15%, 20%, 25%, 30%, 35%, 40%, 45%, or 50%.

Figure 7A:
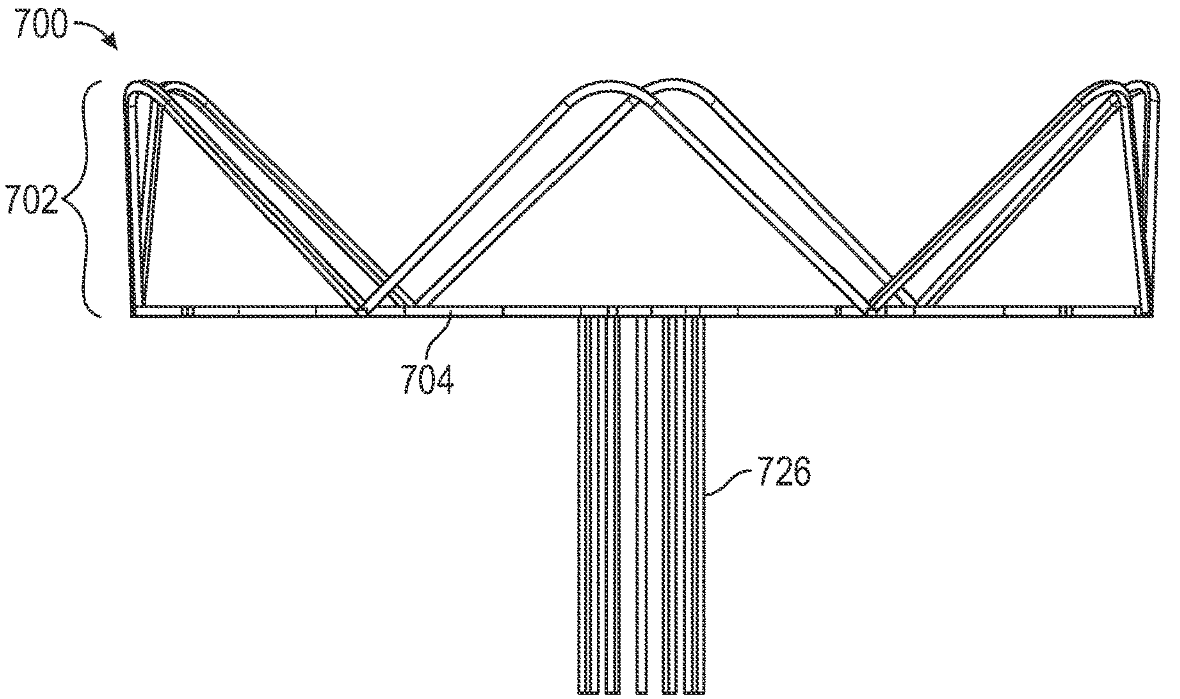
FIG. 7A is a side view of an occlusive device in an expanded configuration, in accordance with embodiments of the present technology.
Figure 7B:
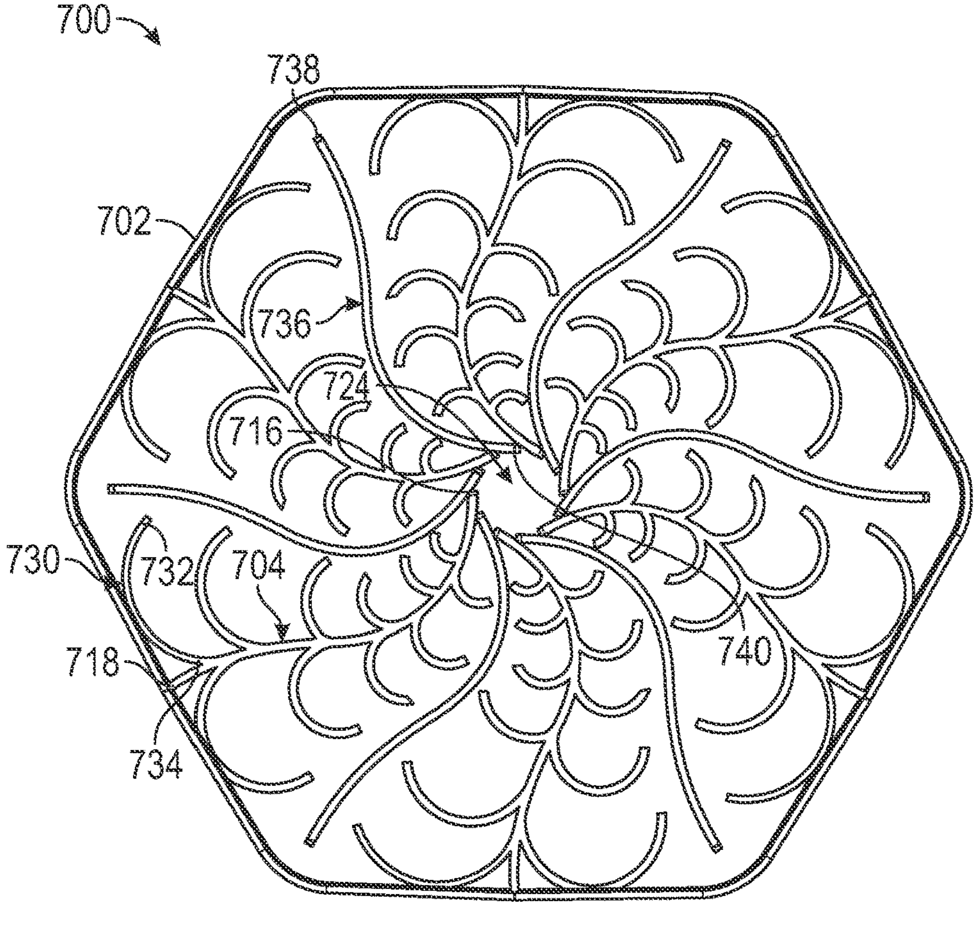
FIG. 7B is a top view of the occlusive device of FIG. 7A.
Figure 7C:
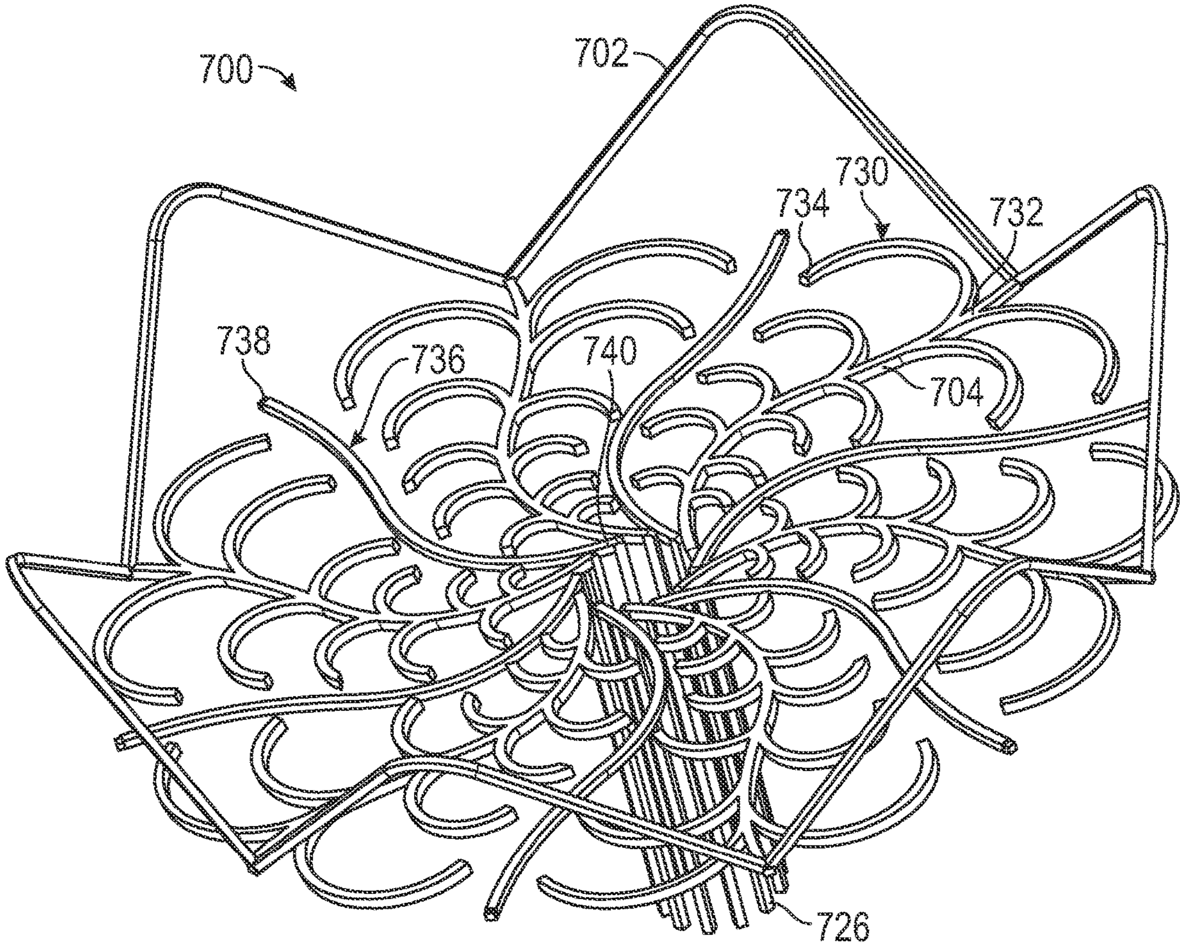
FIG. 7C is an upper perspective view of the occlusive device of FIGS. 7A and 7B.

FIGS. 7A-7C illustrate side, top, and perspective views, respectively, of an occlusive device 700 in its expanded configuration. The device 700 is generally similar to the device 500 of FIGS. 5A-5C, except that the device 700 includes additional secondary curved struts 736 in combination with the primary curved struts 704 which can be similar to the curved struts 504 described above. As illustrated, these secondary curved struts 736 include no protrusions 730 extending therefrom. Additionally, these secondary curved struts 736 are coupled, at a first end region 738, to the primary curved struts 704 near the central opening 724 (either directly connected to these struts or joined together via a hub or other connection element). However, the second end region 740 of each secondary curved strut 736 is free and unconnected to other struts or to the anchor structure 702. The addition of these secondary curved struts 736 can increase the material coverage of the occlusive device compared to the example shown in FIGS. 5A-5C.

With continued reference to FIGS. 7A-7C, the primary curved struts 704 and secondary curved struts 736 alternate radially around the central aperture 724. As such, there are an equal number of primary curved struts 704 and secondary curved struts 736. However, in various embodiments there may be any suitable number of primary curved struts 704 and/or secondary struts 736, including more primary curved struts 704 than secondary struts 736 or vice versa. In some implementations, two or more primary curved struts 704 may be radially adjacent to one another without an intervening secondary curved strut 736, and similarly two or more secondary curved struts 736 can be radially adjacent to one another without an intervening primary curved strut 704.

Figure 8A:
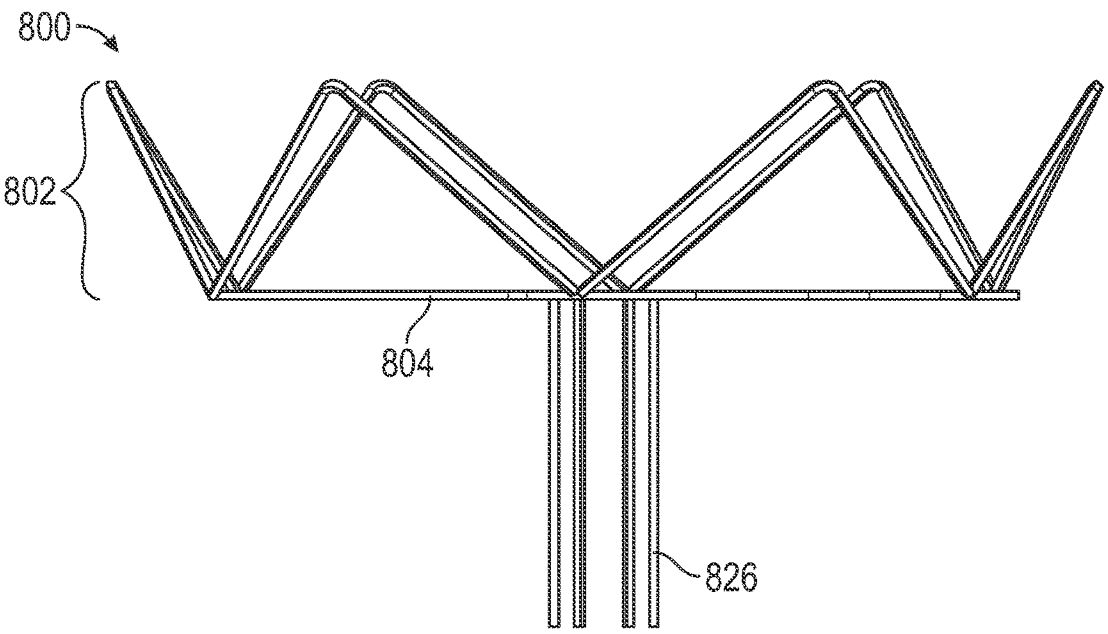
FIG. 8A is a side view of an occlusive device in an expanded configuration, in accordance with embodiments of the present technology.
Figure 8B:
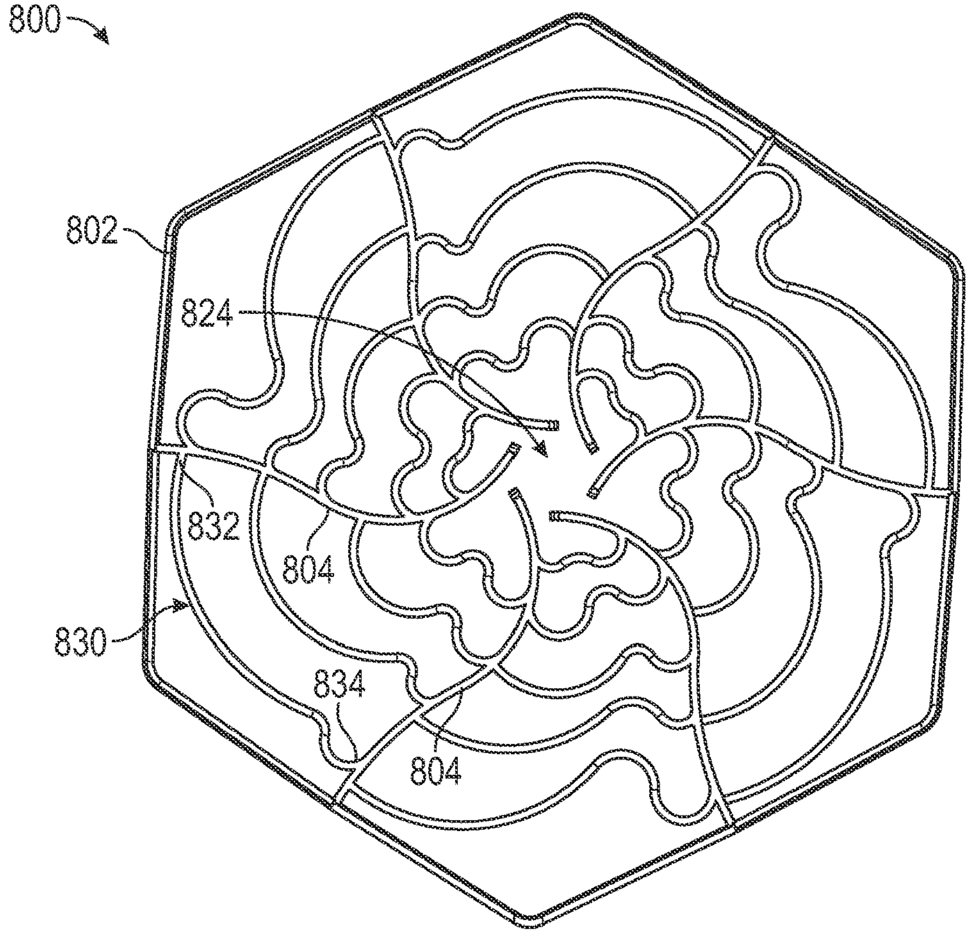
FIG. 8B is a top view of the occlusive device of FIG. 8A.
Figure 8C:
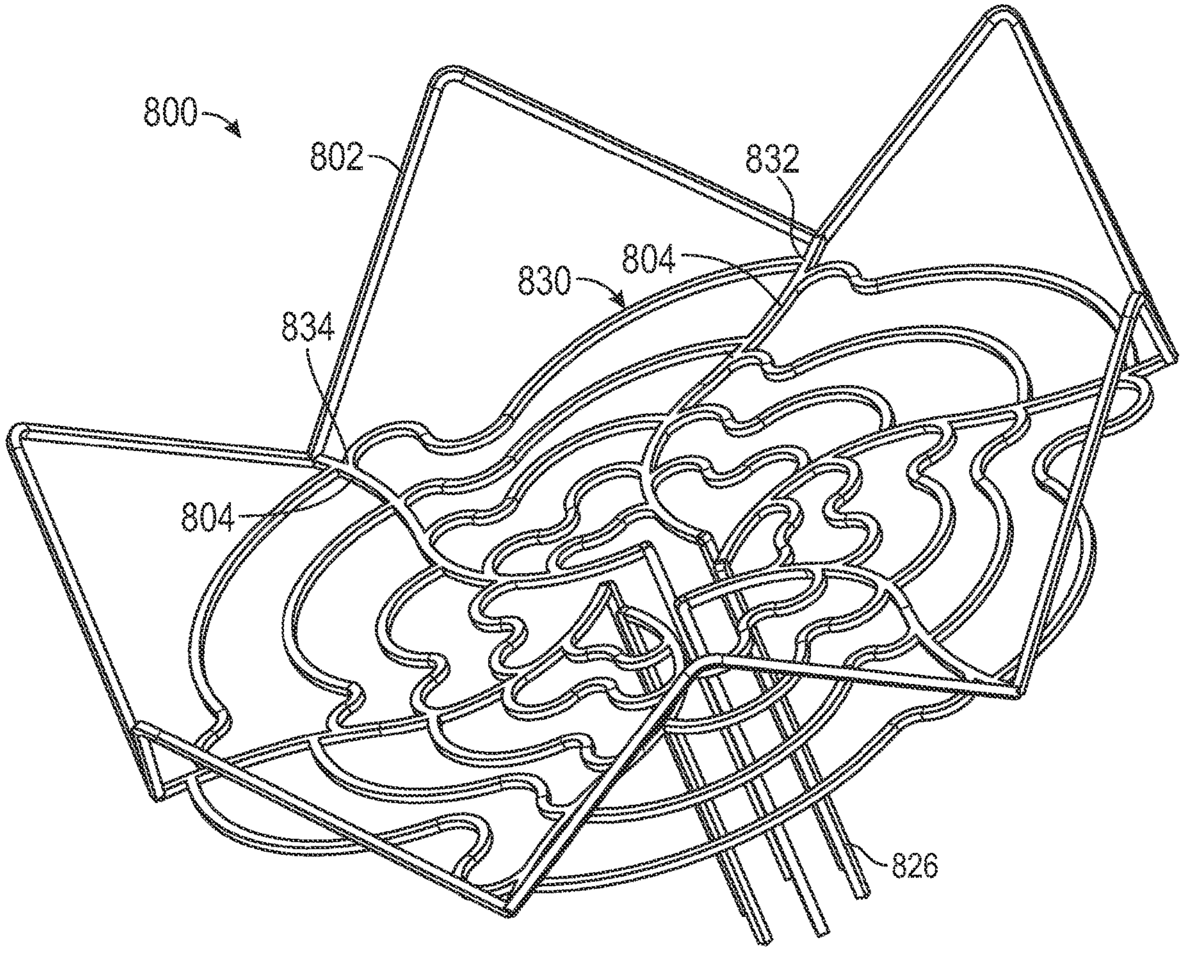
FIG. 8C is an upper perspective view of the occlusive device of FIGS. 8A and 8B.

FIGS. 8A-8C illustrate side, top, and perspective views, respectively, of an occlusive device 800 in its expanded configuration. The device 800 is generally similar to the devices 500 and 700 described above, except that the protrusions 830 of the occlusive device 800 extend between adjacent curved struts 704. For instance, a given protrusion 830 can have a first end 832 coupled to a first curved strut 804 and a second end 834 coupled to another, radially adjacent curved strut 804.

The protrusions 830 can extend in a generally circumferential direction (e.g., annularly or circumferentially extending around the central aperture 824). As illustrated, the protrusions 830 can have undulating, curved, serpentine, sinusoidal, or other profile, with any suitable number of undulations, curves, bends, etc along their respective lengths. In the illustrated example, those protrusions 830 nearer to the central aperture 824 can have more undulations (e.g., be further displaced from a semi-circular arc) than other protrusions 830 that are positioned more radially outwardly. In some implementations, providing protrusions 830 that extend entirely from one curved strut 804 to another curved strut 804 can increase the material coverage of the occlusive device compared to the example shown in FIGS. 5A-5C. Additionally, because the protrusions 830 are secured at each end, the resulting structure may be more stable and less prone to undesired deflection or deformation while implanted within the body.

Conclusion

Although many of the embodiments are described above with respect to systems, devices, and methods for treating a cerebral aneurysm, the technology is applicable to other applications and/or other approaches. For example, the occlusive devices, systems, and methods of the present technology can be used to treat any vascular defect and/or fill or partially fill any body cavity or lumen or walls thereof, such as for parent vessel take down, endovascular aneurysms outside of the brain, arterial-venous malformations, embolization, atrial and ventricular septal defects, patent ductus arteriosus, left atrial appendage, and patent foramen ovale. Additionally, several other embodiments of the technology can have different states, components, or procedures than those described herein. It will be appreciated that specific elements, substructures, advantages, uses, and/or other features of the embodiments described can be suitably interchanged, substituted or otherwise configured with one another in accordance with additional embodiments of the present technology. A person of ordinary skill in the art, therefore, will accordingly understand that the technology can have other embodiments with additional elements, or the technology can have other embodiments without several of the features shown and described above with reference to FIGS. 1A-8C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. An occlusive device for treating an aneurysm, the occlusive device expandable from a low-profile configuration to an expanded configuration, the occlusive device comprising:

an anchor structure extending circumferentially around an opening;

a plurality of spiral struts coupled to the anchor structure and extending over the opening; and a plurality of protrusions extending away from the spiral struts, wherein the plurality of spiral struts and the plurality of protrusions are arranged within a common plane when the occlusive device is in the expanded configuration such that a height defined by each spiral strut or protrusion along a proximal-distal axis is no more than 10% of a radial width defined by the anchor structure, and wherein, in the expanded configuration, the plurality of spiral struts is configured to span a neck of the aneurysm and the anchor structure is configured to engage a wall of the aneurysm, and wherein each of the plurality of protrusions extends laterally away from a respective spiral strut of the plurality of spiral struts within the common plane, with each protrusion comprising a first end coupled to the respective spiral strut of the plurality of spiral struts and a second free end that is not coupled to a spiral strut of the plurality of spiral struts and also not coupled to the anchor structure, each protrusion covering a portion of the opening and thereby occluding blood flow therethrough.

2. The occlusive device of claim 1, further comprising a hub joining the plurality of spiral struts together for connection to a pusher member, wherein each spiral strut comprises a first end region coupled to the hub, and a second end region coupled to the anchor structure.

3. The occlusive device of claim 2, wherein the hub is releasably coupled to a pusher member.

4. The occlusive device of claim 1, wherein the plurality of spiral struts are configured to be contained entirely within the aneurysm with the occlusive device deployed within the aneurysm and in the expanded configuration.

5. The occlusive device of claim 1, wherein the plurality of spiral struts can assume a radially constrained configuration in which a radius of curvature of each spiral strut has a first value, and wherein when the plurality of spiral struts assume a radially unconstrained configuration, the radius of curvature of each spiral strut has a second value larger than the first value, such that when the plurality of spiral struts are released from the radially constrained configuration, the plurality of spiral struts exert radially outwardly directed forces to urge the anchor structure to engage the wall of the aneurysm.

6. The occlusive device of claim 1, wherein the plurality of spiral struts can assume a radially constrained configuration and a radially unconstrained configuration, and wherein a radial distance between opposing ends of each spiral strut is greater in the radially unconstrained configuration than in the radially constrained configuration, such that when the plurality of spiral struts are released from the radially constrained configuration, the plurality of spiral struts exert radially outwardly directed forces to urge the anchor structure to engage the wall of the aneurysm.

7. An occlusive device for treating an aneurysm, the occlusive device comprising:

an anchor structure defining a central opening;

a hub;

a plurality of curved struts arranged in a spiral configuration, each of the curved struts comprising a first end region coupled to the anchor structure and a second end region coupled to the hub such that with the occlusive device in a deployed configuration the plurality of curved struts extend over the central opening, and a plurality of protrusions each comprising a free first end not coupled to a curved strut and a second end that is coupled to a respective curved strut at a position between the first end region and the second end region of the curved strut.

8. The occlusive device of claim 7, wherein, in the deployed configuration, the plurality of curved struts and the plurality of protrusions are arranged in a common plane.

9. The occlusive device of claim 7, wherein the plurality of curved struts are configured to be contained entirely within the aneurysm with the occlusive device deployed within the aneurysm.

10. The occlusive device of claim 7, wherein the plurality of curved struts can assume a radially constrained configuration in which a radius of curvature of each curved strut has a first value, and wherein when the plurality of curved struts assume a radially unconstrained configuration, the radius of curvature of each curved strut has a second value larger than the first value, such that when the plurality of curved struts are released from the constrained configuration, the plurality of curved struts exert radially outwardly directed forces to urge the anchor structure to engage a wall of the aneurysm.

11. The occlusive device of claim 7, wherein the plurality of curved struts can assume a radially constrained configuration and a radially unconstrained configuration, and wherein a radial distance between opposing ends of each curved strut is greater in the radially unconstrained configuration than in the radially constrained configuration, such that when the plurality of curved struts are released from the radially constrained configuration, the plurality of curved struts exert radially outwardly directed forces to urge the anchor structure to engage a wall of the aneurysm.

12. An occlusive device for treating an aneurysm, the occlusive device transformable between a delivery configuration and a deployed configuration, the occlusive device comprising:

a ring-shaped anchor structure configured to engage a wall portion of the aneurysm;

a central hub disposed at a center region of the occlusive device;

a plurality of spiral struts, each spiral strut having a first end coupled to the anchor structure and a second end coupled to the central hub, wherein the plurality of spiral struts extend across an opening defined by the anchor structure; and a plurality of protrusions distributed along the plurality of spiral struts each protrusion comprising a first end coupled to a respective spiral strut of the plurality of spiral struts and a second free end that extends laterally away from the respective spiral strut within a common plane, wherein the second free end is not coupled to the anchor structure, wherein, in the deployed configuration, the plurality of spiral struts and the plurality of protrusions are arranged substantially within the common plane such that the plurality of spiral struts and protrusions span across the opening while the anchor structure extends away from the common plane to engage the wall portion of the aneurysm.

13. The occlusive device of claim 12, wherein the plurality of protrusions extend from the plurality of spiral struts in a direction corresponding to a circumferential direction of the plurality of spiral struts.

14. The occlusive device of claim 12, wherein each spiral strut of the plurality of sprial struts includes protrusions of the plurality of protrusions extending laterally from both sides of the respective spiral strut within the common plane.

15. The occlusive device of claim 12, wherein, in the deployed configuration, at least some of the protrusions of the plurality of protrusions are configured to overlap with adjacent spiral struts of the plurality of spiral struts when viewed along an axis perpendicular to the common plane, thereby increasing coverage across the opening defined by the anchor structure.

16. The occlusive device of claim 12, wherein lengths of the protrusions of the plurality of protrusions are configured to overlap with adjacent spiral struts of the plurality of spiral struts vary according to their radial position relative to the central hub, with the protrusions of the plurality of protrustions positioned further from the central hub having greater lengths than the protrusions of the plurality of protrusions positioned closer to the central hub.

17. The occlusive device of claim 12, wherein the device is formed from a single flat sheet of material that is laser-cut or etched and subsequently heat-set such that the anchor structure extends away from the common plane in the deployed configuration.

18. The occlusive device of claim 12, further comprising a detachment element releasably coupled to the central hub, wherein the detachment element is configured to separate from the central hub upon application of at least one of an electrolytic current, mechanical force, thermal energy, or electromagnetic energy.

* * * * *